US010781469B2

(12) United States Patent
Deng et al.

(10) Patent No.: US 10,781,469 B2
(45) Date of Patent: Sep. 22, 2020

(54) MULTI-MEDIATOR REAGENT FORMULATIONS FOR USE IN ELECTROCHEMICAL DETECTION

(71) Applicant: Omni Biomedical, Inc., Weston, FL (US)

(72) Inventors: David Zhi Deng, Weston, FL (US); Gary T. Neel, York, PA (US)

(73) Assignee: Omni Biomedical, Inc., Weston, FL (US)

(*) Notice: Subject to any disclaimer, the term of this patent is extended or adjusted under 35 U.S.C. 154(b) by 422 days.

(21) Appl. No.: 15/173,211

(22) Filed: Jun. 3, 2016

(65) Prior Publication Data

US 2016/0355862 A1 Dec. 8, 2016

Related U.S. Application Data

(60) Provisional application No. 62/170,995, filed on Jun. 4, 2015.

(51) Int. Cl.
*C12Q 1/00* (2006.01)
*G01N 27/327* (2006.01)

(52) U.S. Cl.
CPC ......... *C12Q 1/006* (2013.01); *G01N 27/3271* (2013.01); *G01N 2333/904* (2013.01)

(58) Field of Classification Search
CPC .......... C12Q 1/00; C12Q 1/001; C12Q 1/004; C12Q 1/005; C12Q 1/006; C12Q 1/26; C12Q 1/34; C12Q 1/54; G01N 27/48; G01N 27/26; G01N 27/327–3274; G01N 33/487; G01N 33/49; A61B 5/14532; A61B 5/14535; A61B 5/14536
See application file for complete search history.

(56) References Cited

U.S. PATENT DOCUMENTS

| | | | | |
|---|---|---|---|---|
| 5,589,326 A | * | 12/1996 | Deng | C07F 15/0026 435/14 |
| 6,033,866 A | * | 3/2000 | Guo | C12Q 1/006 205/263 |
| 8,057,659 B2 | | 11/2011 | Harding et al. | |
| 8,062,490 B2 | | 11/2011 | Bell et al. | |
| 8,207,336 B2 | | 6/2012 | Harding | |
| 8,658,011 B2 | | 2/2014 | Hoashi et al. | |
| 2004/0050717 A1 | * | 3/2004 | Teodorczyk | C12Q 1/004 205/777.5 |

(Continued)

OTHER PUBLICATIONS

International Patent Application No. PCT/US2016/035817, filed Jun. 3, 2016, by OMNI Biomedical, Inc.: International Search Report and Written Opinion, dated Nov. 18, 2016, including Notification of Transmittal (12 pages).

(Continued)

*Primary Examiner* — Maris R Kessel
(74) *Attorney, Agent, or Firm* — Finnegan, Henderson, Farabow, Garrett & Dunner LLP

(57) ABSTRACT

The present disclosure provides, inter alia, mediator formulations for the measurement of an analyte comprising at least one ruthenium compound and at least one osmium compound. Also disclosed are reagent formulations for the measurement of an analyte comprising at least one ruthenium compound and at least one osmium compound. Also disclosed are methods and devices for the measurement of an analyte in a sample.

15 Claims, 9 Drawing Sheets

(56) References Cited

U.S. PATENT DOCUMENTS

| | | | | |
|---|---|---|---|---|
| 2004/0186365 A1* | 9/2004 | Jin | ............... | A61B 5/0002 |
| | | | | 600/365 |
| 2004/0238359 A1* | 12/2004 | Ikeda | ............... | C12Q 1/004 |
| | | | | 204/403.1 |
| 2006/0113187 A1* | 6/2006 | Deng | ............... | C12Q 1/005 |
| | | | | 204/403.01 |
| 2007/0295616 A1* | 12/2007 | Harding | ............... | C12Q 1/004 |
| | | | | 205/777.5 |
| 2010/0227355 A1 | 9/2010 | Bell et al. | | |
| 2013/0081958 A1 | 4/2013 | Jung et al. | | |
| 2013/0084589 A1* | 4/2013 | Kraft | ............... | G01N 27/3273 |
| | | | | 435/14 |
| 2013/0098775 A1* | 4/2013 | Pei | ............... | C12Q 1/006 |
| | | | | 205/777.5 |

OTHER PUBLICATIONS

Ferri, Stefano et al., "Review of Glucose Oxidases and Glucose Dehydrogenases: A Bird's Eye View of Glucose Sensing Enzymes", *J. Diabetes Sci Technol.* 5(5):1068-1076 (2011).

Tsujimura, Seiya et al., "Novel FAD-Dependent Glucose Dehydrogenase for a Dioxygen-Insensitive Glucose Biosensor", *Biosci. Biotechnol. Biochem.* 70(3): 654-659 (2006).

\* cited by examiner

MULTI-MEDIATOR REAGENT FORMULATIONS FOR USE IN ELECTROCHEMICAL DETECTION

This application claims priority from U.S. Provisional Application No. 62/170,995, filed Jun. 4, 2015, which is hereby incorporated by reference in its entirety.

The present disclosure relates to reagents, methods, and devices for the measurement of analytes. The present disclosure is particularly applicable to reagents, methods, and devices for measuring blood analyte levels, such as, for example, glucose.

The long-term health of many lives may depend on accurate measurement of important analytes in biological samples, such as blood glucose levels. Accordingly, meters and test strips utilized in measuring blood glucose levels should be highly reliable. However, due to decreasing sample sizes, the dimensions of the sample chamber and electrodes in the test strip also decreases. This, in turn, may make test strips more prone to smaller manufacturing defects and to damage from subsequent handling.

Accordingly, there is a need for improved mediator formulations with improved sensitivity to the concentration of blood glucose in patient samples for use in measuring systems and methods.

Numerous mediators have been disclosed for use in electrochemical sensors, including transition metal complexes and organic compounds. Although many of these mediators have some properties that could make them desirable for use in electrochemical sensing, they often also have undesirable properties as well.

For example, U.S. Pat. No. 5,589,326, incorporated herein by reference, discloses osmium compounds of Formula I:

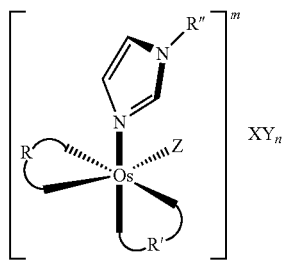

Formula I wherein:
R and R' are the same or different and are selected from 2,2'-bipyridyl, 4,4'-disubstituted-2,2'-bipyridyl, 5,5'-disubstituted-2,2'-bipyridyl, 1,10-phenanthrolinyl, 4,7-disubstituted-1,10-phenanthrolinyl, and 5,6-disubstituted-1,10-phenanthrolinyl, wherein the disubstitution is a methyl, ethyl, or phenyl group;
R and R' are coordinated to Os at their nitrogen atoms;
R" is selected from hydrogen, methyl, and ethyl;
Z is chloro or bromo;
m is +1 or +2;
X is an anion selected from chloride, bromide, iodide, fluoride, tetrafluoroborate, perchlorate, nitrate, sulfate, carbonate, and sulfite;
Y is an anion selected from chloride, bromide, iodide, fluoride, tetrafluoroborate, perchlorate, and nitrate;
n is 1 or 0;
with the proviso that if X is sulfate, carbonate, or sulfite, then n is 0;
and with the proviso that if m is +1, then n is 0, and X is not sulfate, carbonate, or sulfite;
and wherein the aqueous solubility of the compound is greater than about 1 mM.

Previous uses of these compounds as mediators in electrochemical biosensors, such as the biosensor described in U.S. Pat. No. 5,288,636, required high concentrations of at least about 150 mM and preferably, at least about 160 mM of the osmium compound. However, these compounds have poor stability in dry reagent on test strips and create disruptively high background currents at high concentrations, interfering with the ability to read diagnostic signals.

Other mediators are known. For example, ruthenium hexammine trichloride ($Ru(NH_3)_6Cl_3$) is a mediator with excellent stability but displays extremely slow mediation kinetics for many redox enzymes, particularly flavin adenine dinucleotide-dependent glucose dehydrogenase (FAD-GDH).

To overcome the shortcomings present in single mediator systems, previous studies have sought to combine multiple mediators to obtain improved properties. However, work in this area has been limited and suffers from unpredictable and erratic results.

For example, U.S. Pat. No. 8,207,336 discloses combinations of specific osmium complexes with ferrocyanide. However, the osmium complexes of U.S. Pat. No. 8,207,336 were limited by poor solubility (<1 mM) and when combined with ferricyanide, still resulted in a significant background current of about 2 µA. Furthermore, ferricyanide is known to produce higher background current under thermal stress resulting in poor long-term stability.

Additionally, previous combinations of ruthenium hexammine with certain organic mediators such as phenazine methosulfate and Meldola's Blue have been known. However, these organic mediators have poor solubility (e.g., about 1-2 mM) which may limit their effectiveness in maximizing dose response sensitivity.

Accordingly, there is a need for novel multi-mediator formulations that overcome the drawbacks of single-mediator systems.

SUMMARY

The present disclosure is based, at least in part, on the unexpected discovery that the combination in prescribed amounts of ruthenium hexammine with certain osmium compounds results in a synergistic effect, providing a multi-mediator formulation that overcomes the shortcomings of each individual mediator to give a desirable combination of properties. It has been found that this novel multi-mediator formulation can be successfully used with flavin adenine dinucleotide-dependent glucose dehydrogenase (FAD-GDH) with surprisingly low background current (e.g. about 0.1 □A), providing an improvement over each mediator used alone and in the prior art as a whole. It has also been discovered that this novel multi-mediator formulation can be successfully used with glucose oxidase (GOX) with surprisingly low oxygen interference and minimal measurement bias, providing an improvement over each mediator used alone and in the prior art as a whole. The synergistic effects of this multi-mediator formulation are applicable to a wide range of analyte/enzyme pairings, and are not limited those described or exemplified herein.

In some aspects, the present disclosure provides a mediator formulation comprising multiple electron mediators (i.e., a multiple mediator or multi-mediator formulation), for example, two electron mediators, resulting in a synergistic effect for improved determination of an analyte, such as glucose, in a sample.

In some aspects, the present disclosure provides a mediator formulation for detecting an analyte comprising at least one osmium compound and at least one ruthenium compound.

In some aspects, the present disclosure provides a mediator formulation for detecting an analyte, comprising:
  at least one ruthenium compound; and
  at least one osmium compound selected from a compound of Formula I:

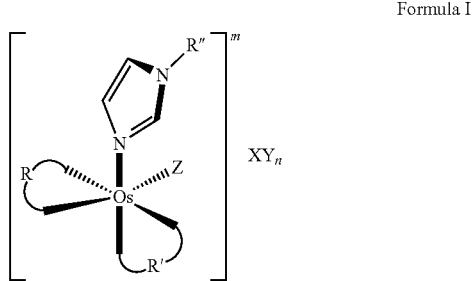

Formula I wherein:
R and R' are the same or different and are selected from 2,2'-bipyridyl, 4,4'-disubstituted-2,2'-bipyridyl, 5,5'-disubstituted-2,2'-bipyridyl, 1,10-phenanthrolinyl, 4,7-disubstituted-1,10-phenanthrolinyl, and 5,6-disubstituted-1,10-phenanthrolinyl, wherein the disubstitution is a methyl, ethyl, or phenyl group;
R and R' are coordinated to Os at their nitrogen atoms;
R" is selected from hydrogen, methyl, and ethyl;
Z is chloro or bromo;
m is +1 or +2;
X is an anion selected from chloride, bromide, iodide, fluoride, tetrafluoroborate, perchlorate, nitrate, sulfate, carbonate, and sulfite;
Y is an anion selected from chloride, bromide, iodide, fluoride, tetrafluoroborate, perchlorate, and nitrate;
n is 1 or 0;
with the proviso that if X is sulfate, carbonate, or sulfite, then n is 0;
and with the proviso that if m is +1 and n is 0, X is not sulfate, carbonate, or sulfite;
and wherein the aqueous solubility of the compound is greater than about 1 mM.

In some aspects, the present disclosure provides a mediator formulation comprising ruthenium hexammine trichloride ($Ru(NH_3)_6Cl_3$) and $[Os(III)(bpy)_2imCl]Cl_2$, which has the following structure:

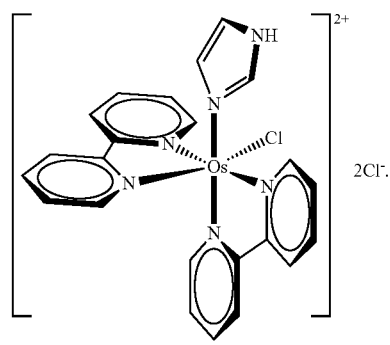

In some aspects, the present disclosure provides a reagent formulation comprising:
  a mediator formulation comprising at least one osmium compound and at least one ruthenium compound; and
  an oxidoreductase optionally comprising a coenzyme and/or cofactor.

In some aspects, the reagent formulation optionally further comprises one or more components selected from the following: binding agents, thickening agents, buffering agents, wetting agents (such as, for example, surfactants), and stabilizers.

In some aspects, the present disclosure provides a reagent formulation for coating on a test strip to form a reagent layer for testing a blood sample. Any reagent formulation described herein may be coated on a test strip to form a reagent layer for testing a blood sample. In some aspects, the reagent formulation for coating a test strip comprises an oxidoreductase optionally comprising a coenzyme and/or cofactor, and a mediator formulation comprising at least one osmium compound and at least one ruthenium compound.

In other aspects, the present disclosure provides a method for determination of an analyte in a sample by using any mediator formulation and/or reagent formulation as described herein. In some aspects, the analyte is glucose.

In other aspects, the present disclosure provides a test strip for testing a blood sample. The test strip comprises a base, at least one working electrode, at least one counter electrode, and a reagent layer. The reagent layer may be formed from any reagent formulation as described herein. In some aspects, the reagent layer comprises a glucose oxidoreductase optionally comprising a flavin nucleoside and/or a nicotinamide nucleotide coenzyme, and a mediator formulation comprising at least one osmium compound and at least one ruthenium compound.

In other aspects, the present disclosure provides a method of making a test strip for testing a blood sample. The method comprises applying a first electrode on a base; applying a second electrode on the base; and applying a reagent layer on the base covering at least a portion of at least first or second electrode. The reagent layer may be formed using any reagent formulation as described herein. In some aspects, the reagent layer comprises a glucose oxidoreductase optionally comprising a flavin nucleoside coenzyme and/or a nicotinamide nucleotide coenzyme, and a mediator formulation comprising at least one osmium compound and at least one ruthenium compound.

In other aspects, the present disclosure provides for a meter for use in combination with a test strip for measuring a glucose level in a blood sample applied to a test strip, said test strip comprising a base, a working electrode, a counter electrode, and at least one reagent layer, wherein the at least one reagent layer comprises a glucose oxidoreductase optionally comprising a flavin adenine dinucleotide and/or nicotinamide adenine dinucleotide(phosphate), and a mediator formulation comprising at least one osmium compound and at least one ruthenium compound. The meter comprises a port for receiving said test strip, a processor, a display and at least one voltage source for applying at least a first voltage between said working and counter electrodes when said test strip is inserted.

In other aspects, the present disclosure provides a continuous analyte monitoring system for monitoring an analyte (e.g., glucose) using a mediator formulation comprising at least one ruthenium compound and at least one osmium compound and/or a reagent formulation comprising an oxidoreductase optionally comprising a coenzyme and/or cofactor, and a mediator formulation comprising at least one osmium compound and at least one ruthenium compound. In some aspects, the continuous analyte system may be configured to detect one or more analyte levels, (e.g., glucose).

In some aspects, the present disclosure provides a continuous analyte monitoring system comprising a continuous analyte sensor that may be configured to produce a data signal indicative of an analyte concentration in a host during exposure of the sensor to a biological sample. In some aspects, the continuous analyte sensor is implanted in a host, for example, under the skin, for continuous in-vivo monitoring. In some aspects, the continuous analyte sensor continuously detects one or more analyte levels in vivo and transfers the detected analyte level information at predetermined time intervals to data processing devices for monitoring, diagnosis, and/or analysis It is to be understood that both the foregoing general description and the following detailed description are exemplary and explanatory only and are not restrictive of the invention, as claimed.

The accompanying figures which are incorporated in and constitute a part of this specification, illustrate one or several embodiment(s) of the invention and together with the description, serve to explain the principles of the invention.

DEFINITIONS

Figure 1:
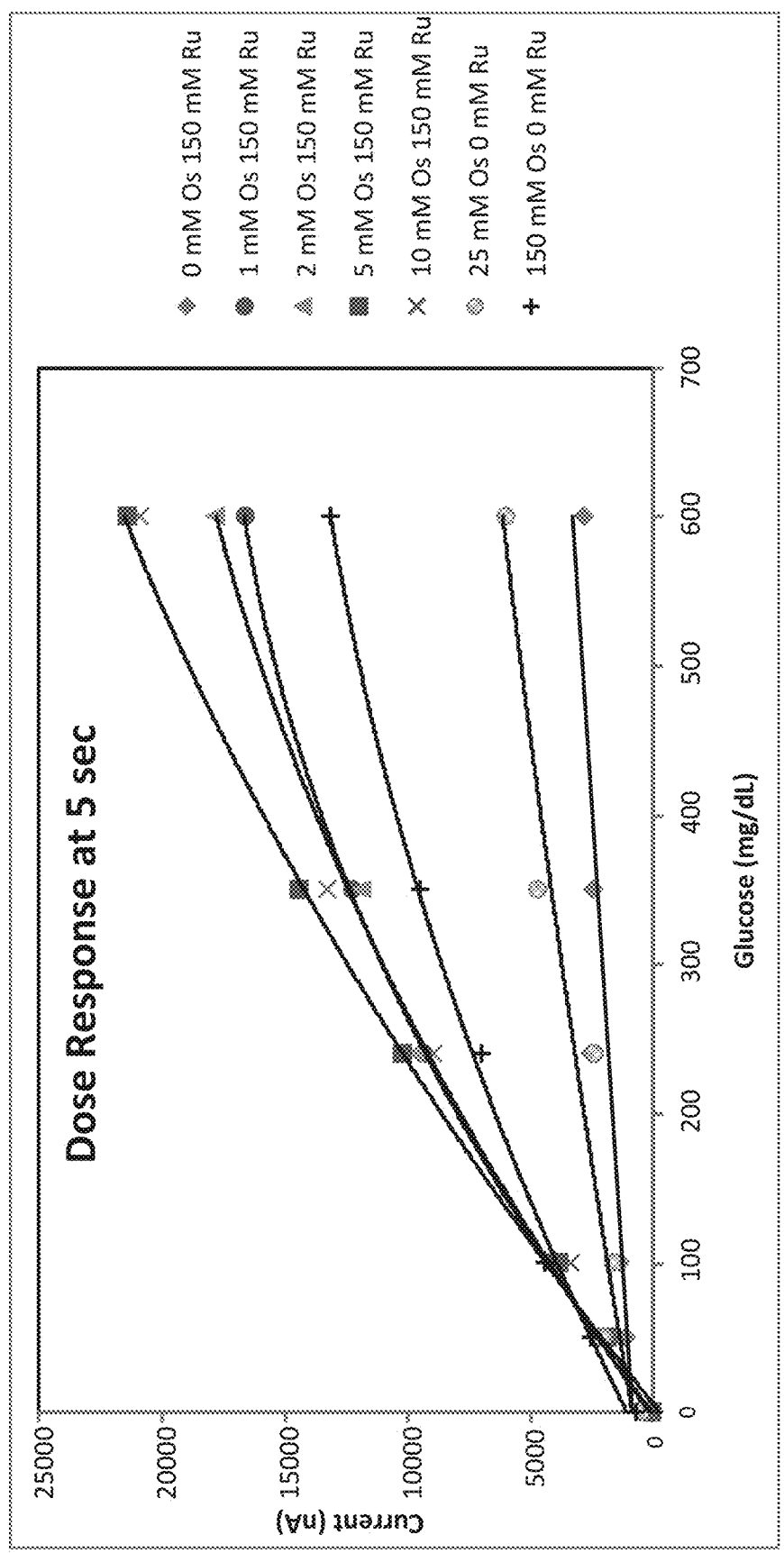
FIG. 1 is a graph of measured current as a function of glucose concentration for the following mediator formulations with FAD-GDH: (1) a single-mediator formulation comprising ruthenium hexammine trichloride at 150 mM; (2) single-mediator formulations comprising [Os(III)(bpy)$_2$imCl]Cl$_2$ at 25 mM and 150 mM; and, (3) multi-mediator formulations comprising ruthenium hexammine trichloride at 150 mM and [Os(III)(bpy)$_2$imCl]Cl$_2$ at 1, 2, 5, and 10 mM.

As used herein, the following words, phrases and symbols are generally intended to have the meanings as set forth below, except to the extent that the context in which they are used indicates otherwise. The following abbreviations and terms have the indicated meanings throughout.

As used herein, a "sample" may include a composition containing an unknown amount of an analyte (e.g., glucose) of interest. Typically, a sample for electrochemical analysis is in liquid form, and preferably the sample is an aqueous mixture. A sample may be a biological sample, such as blood, urine or saliva. A sample may be a derivative of a biological sample, such as an extract, a dilution, a filtrate, or a reconstituted precipitate.

As used herein, an "analyte" may include a material of interest in a sample and may be a chemical or biological significance. Non-limiting examples of analytes include glucose, cholesterol, hemoglobin A$_{1C}$, fructose, alcohol, lactate, triglycerides, creatine, creatinine, bilirubin, uric acid, amino acids, ketones, coagulation factors, and the like.

As used herein, a "mediator" or "electron mediator" may include a substance that can be oxidized or reduced and that can transfer one or more electrons between a first substance and a second substance. A mediator is a reagent in an electrochemical analysis and is not the analyte of interest. In a simple system, the mediator undergoes a redox reaction with the oxidoreductase after the oxidoreductase has been reduced or oxidized through its contact with an appropriate substrate. This oxidized or reduced mediator then undergoes the opposite reaction at the electrode and is regenerated to its original oxidation number. A mediator may be used as a single agent or used in combination with one or more other mediators as a multiple mediator formulation. In some non-limiting embodiments, a multiple mediator formulation may comprise an osmium complex and a ruthenium complex. In some non-limiting embodiments, a multiple mediator formulation may [Os(III)(bpy)$_2$imCl]Cl$_2$ and ruthenium hexammine trichloride.

As used herein, an "oxidoreductase" may include any enzyme that facilitates the oxidation or reduction of a substrate, such as, for example, an analyte. Oxidoreductases may include "oxidases," which facilitate oxidation reactions in which molecular oxygen is the electron acceptor; "reductases," which facilitate reduction reactions in which the analyte is reduced and molecular oxygen is not the analyte; and "dehydrogenases," which facilitate oxidation reactions in which molecular oxygen is not the electron acceptor. Non-limiting examples of oxidoreductases include glucose dehydrogenase, glucose oxidase, cholesterol oxidase, cholesterol esterase, bilirubin oxidase, fructosyl amino acid oxidase, fructosyl peptide oxidase, neutral proteinase, lactate dehydrogenase, lactate oxidase, pyruvate oxidase, alcohol dehydrogenase, lipoprotein lipase, glyceral kinase, alcohol oxidase, uricase, and the like.

In some embodiments, the oxidoreductase may optionally comprise a cofactor and/or coenzyme. Non-limiting examples of enzymes comprising a cofactor and/or coenzyme include flavin adenine dinucleotide-dependent glucose dehydrogenase (FAD-GDH), nicotinamide adenine dinucleotide(phosphate)-dependent glucose dehydrogenase (NAD(P)-GDH), pyrroloquinoline quinone glucose dehydrogenase (PQQ-GDH), and glucose oxidase (GOX), which comprises flavin adenine dinucleotide in its center. In some embodiments, the oxidoreductase comprises a flavin nucleoside coenzyme or cofactor and is selected from flavin adenine dinucleotide-dependent glucose dehydrogenase (FAD-GDH) and glucose oxidase (GOX).

As used herein, a "coenzyme" may include non-protein compounds that facilitate the functioning of an enzyme. Coenzymes may include non-protein redox prosthetics. Coenzymes of the present disclosure are preferably complex organic or metalloorganic molecules that are linked covalently or non-covalently to an enzyme and are changed, for example, oxidized or reduced, by the conversion of the analyte. Non-limiting examples of coenzymes are flavin, nicotinamide and quinone derivatives, such as, for example: flavin nucleoside derivatives such as FAD, FADH$_2$, FMN, FMNH$_2$, etc.; nicotinamide nucleotide derivatives such as, for example, NAD(P), NAD$^+$, NADH/H$^+$, NADP$^+$, NADPH/H$_2$; or ubiquinones such as, for example, coenzyme Q or PQQ. In some embodiments of the present disclosure the coenzyme is a flavin nucleoside. In some embodiments of the present disclosure, the coenzyme is a nicotinamide nucleotide.

As used herein, a "transition metal complex" may comprise a central atom or ion and a surrounding array of bound molecules or ions, which are known as ligands or complexing agents. Transition metal complexes may include organotransition metal complexes (such as ferricyanide (III) and its reduced ferrocyanide (II) counterpart), or complexes where non-metal atoms other than carbon, such as heteroatoms (e.g. N, S, O, and P), are datively bonded to the transition metal center. Non-limiting examples of transition metal complexes include osmium complexes (e.g. compounds of Formula I), ruthenium complexes (e.g. ruthenium hexammine complexes), and iron complexes.

As used herein, a "ruthenium compound" may include ruthenium complexes. The ligand(s) of the ruthenium complex is/are not particularly limited as long as the ruthenium complex functions as a mediator. Non-limiting examples of ligands, which may be optionally substituted, include bipyridyl, phenanthroline, imidazole, thiolene, thiolate, thioether, sulfide, porphyrins, pyrrole, pyrrazole, thiazole, diazole, triazole, picolinate, carboxylate, oxo, and quinone. Non-limiting examples of monodentate ligands, which may be optionally substituted, include hydrates/hydroxo, aminates, acetates, thiolates, halides, thiocyanates, and cyanides. Non-limiting examples of multidentate ligands, which may be optionally substituted, include aminoacetates, ethylenediaminetetraacetic acid, hydroxyethylethylenediamine triacetic acid, nitrilotriacetic acid, β-alaninediacetic acid, methyleneglycine diacetic acid, iminodisuccinate, glutamate N,N'-bisdiacetic acid, ethylenediamine disuccinic acid, diethylenetriaminepentaacetic acid, polyethers, polycarboxylates, phosphonates, and polyamines. In some embodiments of the present disclosure, a ruthenium compound may be expressed as $[Ru(NH_3)_5X]^{n+}$ wherein X may be NH$_3$, halogen (e.g. Cl$^-$, F$^-$, Br$^-$, I$^-$), CN, pyridine, nicotine amide, and H$_2$O, and wherein n+ represents the overall charge. In some embodiments of the present disclosure, the ruthenium compound is a ruthenium hexammine complex. In some embodiments of the present disclosure, the ruthenium compound is ruthenium hexammine trichloride.

As used herein, an "osmium compound" may include osmium complexes. The ligand(s) of the osmium complex is/are not particularly limited as long as the osmium complex functions as a mediator. Non-limiting examples of ligands, which may be optionally substituted, include bipyridyl, phenanthroline, imidazole, thiolene, thiolate, thioether, sulfide, porphyrins, pyrrole, pyrrazole, thiazole, diazole, triazole, picolinate, carboxylate, oxo, and quinone. Non-limiting examples of monodentate ligands, which may be optionally substituted, include hydrates/hydroxo, aminates, acetates, thiolates, halides, thiocyanates, and cyanides. Non-limiting examples of multidentate ligands, which may be optionally substituted, include aminoacetates, ethylenediaminetetraacetic acid, hydroxyethylethylenediamine triacetic acid, nitrilotriacetic acid, β-alaninediacetic acid, methyleneglycine diacetic acid, iminodisuccinate, glutamate N,N'-bisdiacetic acid, ethylenediamine disuccinic acid, diethylenetriaminepentaacetic acid, polyethers, polycarboxylates, phosphonates, and polyamines. In some embodiments of the present disclosure, the osmium compound is a compound of Formula I. In some embodiments of the present disclosure, the osmium compound is [Os(III)(bpy)$_2$imCl]Cl$_2$.

As used herein, the term "about" is intended to mean approximately, in the region of, roughly or around. When the term "about" is used in conjunction with a numerical range, it modifies that range by extending the boundaries above and below the numerical values set forth. In general, the term "about" is intended to modify a numerical value above and below the stated value by a variance of <10%.

DETAILED DESCRIPTION

Each aspect, embodiment or feature described herein may be combined with any other aspect(s), embodiment(s) or feature(s) unless clearly indicated to the contrary.

The present disclosure utilizes the synergistic effect from a combination of mediators to overcome the shortcomings of each individual mediator to give a desirable combination of properties. In some embodiments, a synergistic effect results from the combination of a ruthenium mediator and an osmium mediator. One exemplary, non-limiting mediator formulation comprises both ruthenium hexammine trichloride (Ru(NH$_3$)$_6$Cl$_3$) and [Os(III)(bpy)$_2$imCl]Cl$_2$ as electron mediators, which may be paired with an oxidoreductase to form a reagent formulation for detecting an analyte.

The reagent formulation can optionally comprise additional excipients such as, for example, wetting agents binding agents, thickening agents, stabilizing agents, and buffering agents. One exemplary, non-limiting reagent formulation comprising additional excipients is provided below:
(i) about 50 mM phosphate buffer;
(ii) about 10,000 U/mL FAD-GDH;
(iii) about 150 mM ruthenium hexammine trichloride ($Ru(NH_3)_6Cl_3$);
(iv) about 1 mM to about 10 mM, preferably about 5 mM, $[Os(III)(bpy)_2imCl]Cl_2$;
(v) about 0.25% w/v hydroxypropyl methylcellulose;
(vi) about 0.06% v/v Triton X-100; and
(vii) pH of about 6.30.

$[Os(III)(bpy)_2imCl]Cl_2$ possesses many desirable qualities for an electron mediator. For example, $[Os(III)(bpy)_2imCl]Cl_2$ has a low oxidation potential of about 150 mV (relative to Ag/AgCl reference electrode). The low oxidation potential of $[Os(III)(bpy)_2imCl]Cl_2$ enables an electrochemical biosensor to operate at potentials where interference from electroactive species, such as bilirubin, acetaminophen, ascorbic acid and uric acid, are low. $[Os(III)(bpy)_2imCl]Cl_2$ also has a fast rate of transfer from FAD-GDH relative to the rate of reaction of the reduced enzyme with oxygen. This enables the mediator to compete more efficiently with interfering species in capturing electrons from the enzyme's redox center. Furthermore, $[Os(III)(bpy)_2imCl]Cl_2$ benefits from slow oxidation of osmium by oxygen, which minimizes error in physiological assays resulting from oxidation of the mediator by molecular oxygen. Additionally, $[Os(III)(bpy)_2imCl]Cl_2$ displays excellent solubility in aqueous medium (maximum solubility is about 180 mM), enabling concentrations above 1 mM, preferably, 5 mM. It is favorable for the mediator used in an electrochemical biosensor to have good solubility in aqueous medium because many important analytical samples, such as whole blood or blood serum, are aqueous based.

However, $[Os(III)(bpy)_2imCl]Cl_2$ has poor stability in dry reagent on test strips and suffers from high background current at high concentrations.

Ruthenium hexammine has a low oxidation potential of about 0 mV (relative to Ag/AgCl reference electrode) and excellent stability that results in a very low background current even at high concentrations (e.g. about 150 mM). However, ruthenium hexammine has an extremely slow rate of reaction with the electroactive center of some oxidoreductases, for example, FAD-GDH, that hinders its use as a suitable electron mediator.

Figure 2:
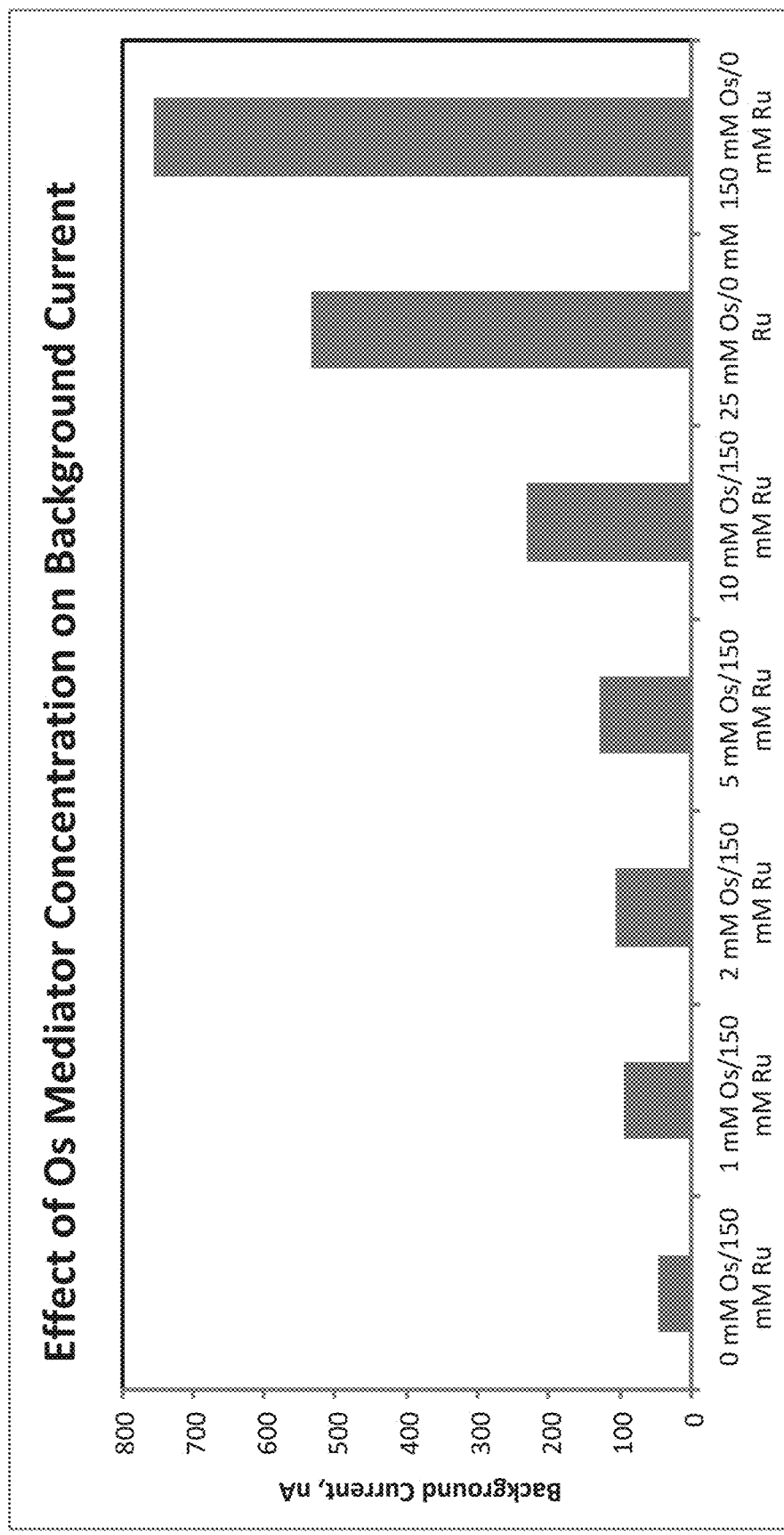
FIG. 2 is a comparison of the background current of single mediator systems (comprising [Os(III)(bpy)$_2$imCl]Cl$_2$) and multi-mediator systems (comprising ruthenium hexammine trichloride and [Os(III)(bpy)$_2$imCl]Cl$_2$) with FAD-GDH.

Surprisingly, it has been found that ruthenium hexammine can be utilized as a mediator for FAD-GDH if used in combination with $[Os(III)(bpy)_2imCl]Cl_2$. The combination of ruthenium hexammine and $[Os(III)(bpy)_2imCl]Cl_2$ provides a synergistic effect that overcomes the shortcomings of each mediator individually. While not wishing to be bound by a particular theory, it is thought that utilizing a large concentration of ruthenium hexammine (preferably about 150 mM) with a relatively low concentration of $[Os(III)(bpy)_2imCl]Cl_2$ (preferably about 5 mM) reduces the impact on mediator formulation stability and minimizes background current. As evident from FIG. 2, a combination of about 150 mM $Ru(NH_3)_6Cl_3$ and about 5 mM $[Os(III)(bpy)_2imCl]Cl_2$ results in a background current of about 100 nA, a significant improvement from using $[Os(III)(bpy)_2imCl]Cl_2$ alone. Furthermore, FIG. 1 shows that the dose response of this mediator formulation (150 mM $Ru(NH_3)_6Cl_3$ and 5 mM $[Os(III)(bpy)_2imCl]Cl_2$) is higher than either $Ru(NH_3)_6Cl_3$ or $[Os(III)(bpy)_2imCl]Cl_2$ alone. In fact, the response slope with the mediator formulation (150 mM $Ru(NH_3)_6Cl_3$ and 5 mM $[Os(III)(bpy)_2imCl]Cl_2$) is increased by about 8 times as compared to $Ru(NH_3)_6Cl_3$ alone. Accordingly, a mediator formulation comprising both a ruthenium mediator and an osmium mediator provides a synergistic combination of desirable properties.

Figure 3:
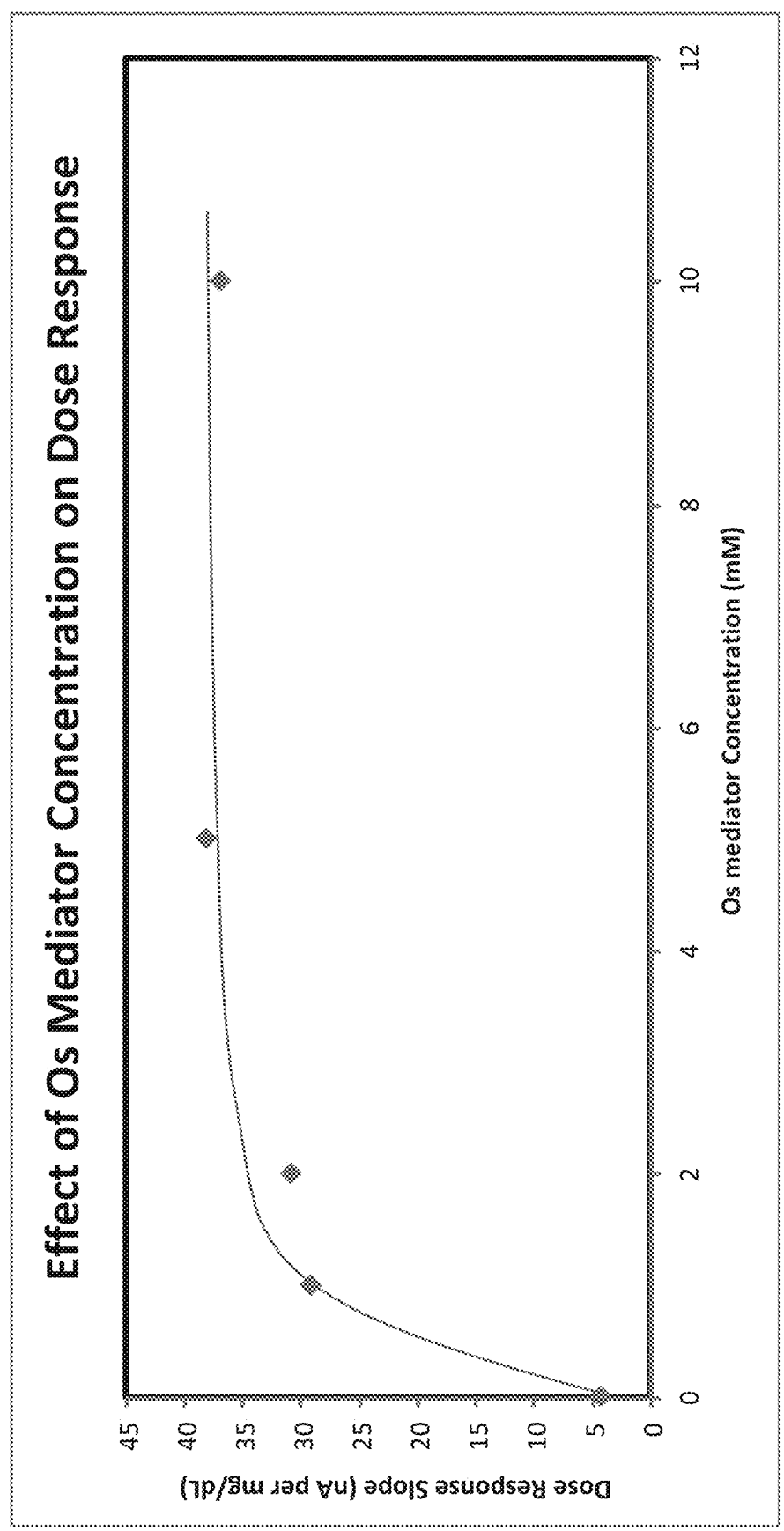
FIG. 3 is a graph of the effect of [Os(III)(bpy)$_2$imCl]Cl$_2$ concentration on dose response for a multi-mediator formulation comprising Ru(NH$_3$)$_6$Cl$_3$ and [Os(III)(bpy)$_2$imCl]Cl$_2$ with FAD-GDH.

In some aspects of the disclosure, the concentration of osmium compound should be kept low to reduce the impact on mediator formulation stability. From FIG. 3, it appears that 5 mM of $[Os(III)(bpy)_2imCl]Cl_2$ is sufficient to achieve optimal dose response, after which the effect of osmium compound concentration plateaus.

In addition to glucose dehydrogenase (GDH), glucose oxidase (GOX) is another glucose oxidoreductase that has been utilized for determining glucose concentrations. Although GOX displays favorable properties such as high thermostability and high glucose sensitivity, glucose measurements with this enzyme are susceptible to oxygen ($O_2$) interference since oxygen is able to function as an electron acceptor for GOX. To minimize $O_2$ interference in GOX systems, mediators such as ferrocene and ferricyanide are typically used to compete with $O_2$. Nonetheless, increased partial pressure of $O_2$ ($pO_2$) in blood samples often results in considerable measurement bias, leading to over- or underestimated blood glucose values. These biases can result in undetected hypo- or hyperglycemic events, which can adversely affect the health of a patient.

Figure 4:
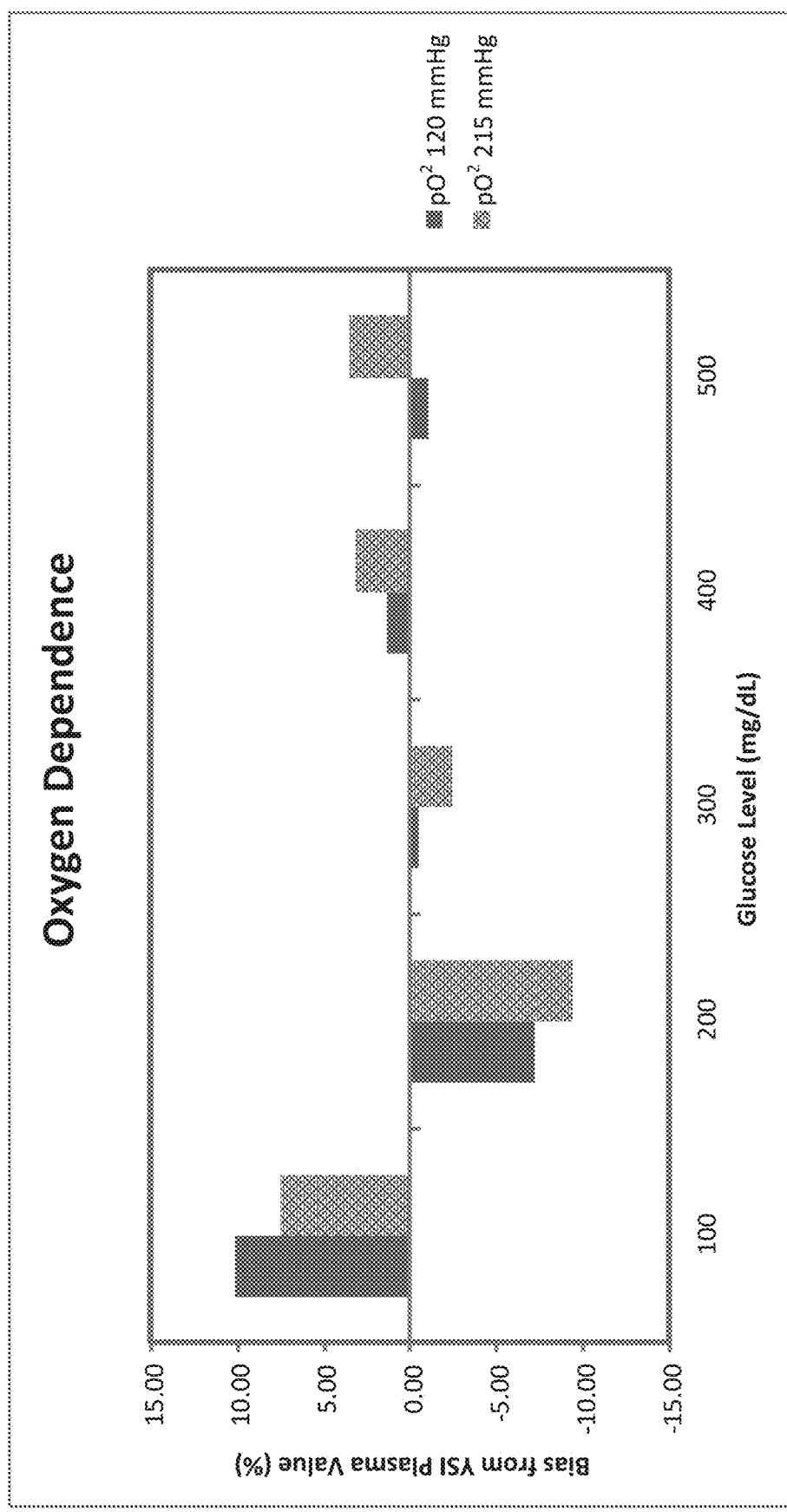
FIG. 4 is a graph of the measurement bias as a function of glucose concentration for a reagent formulation comprising glucose oxidase (GOX) and a multi-mediator formulation comprising 150 mM of Ru(NH$_3$)$_6$Cl$_3$ and 5 mM of [Os(III)(bpy)$_2$imCl]Cl$_2$ at partial pressures of oxygen (pO$_2$) values of 120 mm Hg and 215 mm Hg.
Figure 6:
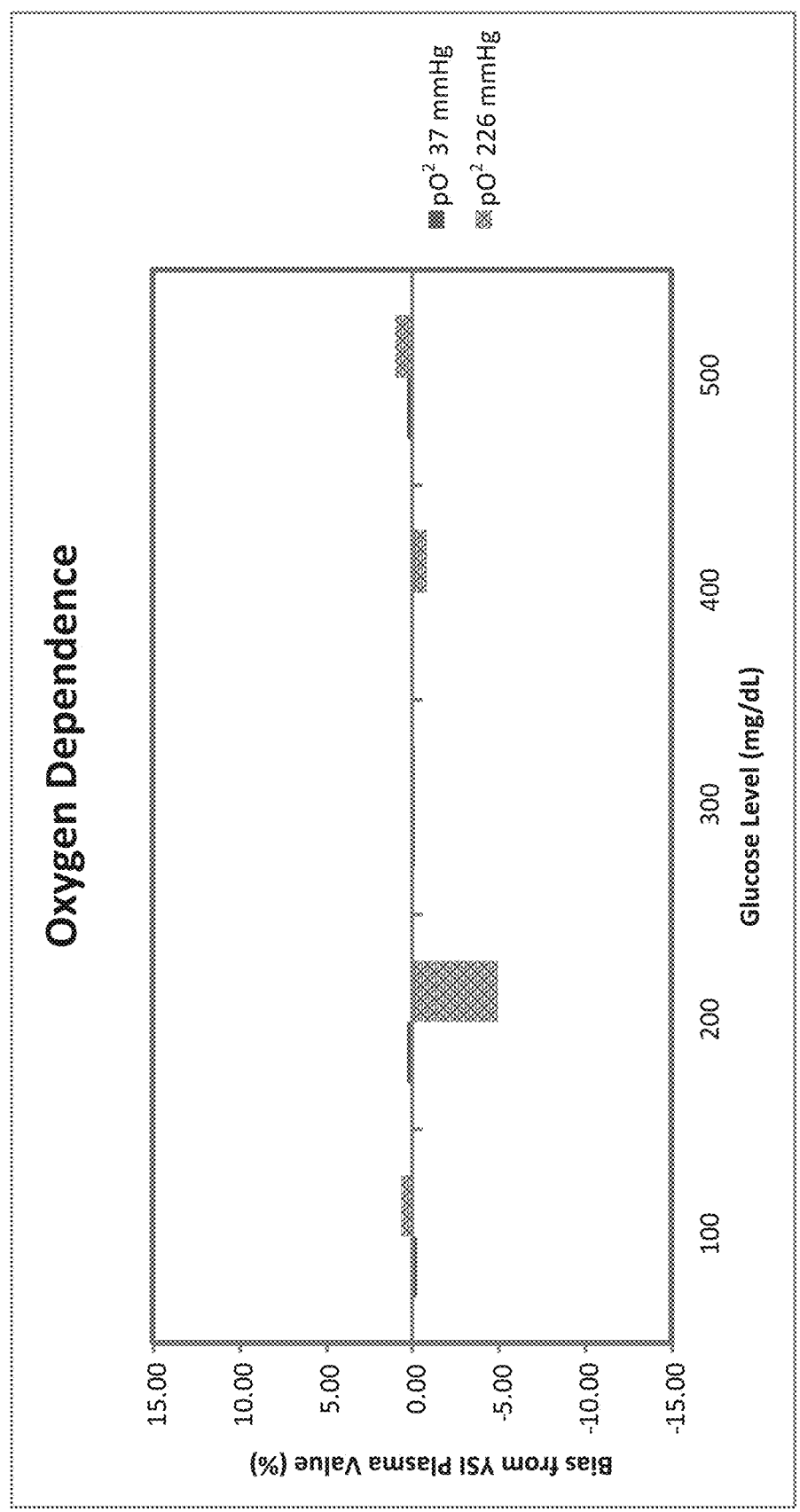
FIG. 6 is a graph of the measurement bias as a function of glucose concentration for a reagent formulation comprising FAD-GDH and a multi-mediator formulation comprising 150 mM of Ru(NH$_3$)$_6$Cl$_3$ and 5 mM of [Os(III)(bpy)$_2$imCl]Cl$_2$ under partial pressures of oxygen (pO$_2$) of 37 mm Hg and 226 mm Hg.

Surprisingly, it has been found that a mediator formulation comprising both a ruthenium mediator and an osmium mediator (e.g., $Ru(NH_3)_6Cl_3$ and $[Os(III)(bpy)_2imCl]Cl_2$) can be successfully used with GOX with minimal $O_2$ interference and low measurement bias at high $pO_2$ values (e.g., 120-215 mm Hg). While not wishing to be bound by a particular theory, it is thought that the mediator formulation demonstrates very fast reaction kinetics with GOX and is able to outcompete $O_2$ as an electron acceptor. As seen in FIG. 4, using a mediator formulation comprising 150 mM $Ru(NH_3)_6Cl_3$ and 5 mM $[Os(III)(bpy)_2imCl]Cl_2$ with GOX at $pO_2$ values as high as 120 and 215 mm Hg resulted in measurement biases between about −10% to about +10% of the actual glucose concentration. At glucose levels of 300 mg/dL and higher, the measurement biases decreased to between about −1% to about +1% at $pO_2$ 120 mm Hg and between about −4% to about +4% at $pO_2$ 215 mm Hg. Notably, these results are similar to the measurement biases in a FAD-GDH system (see FIG. 6), which is $O_2$-insensitive as GDH is unable to utilize $O_2$ as an electron acceptor.

Figure 5:
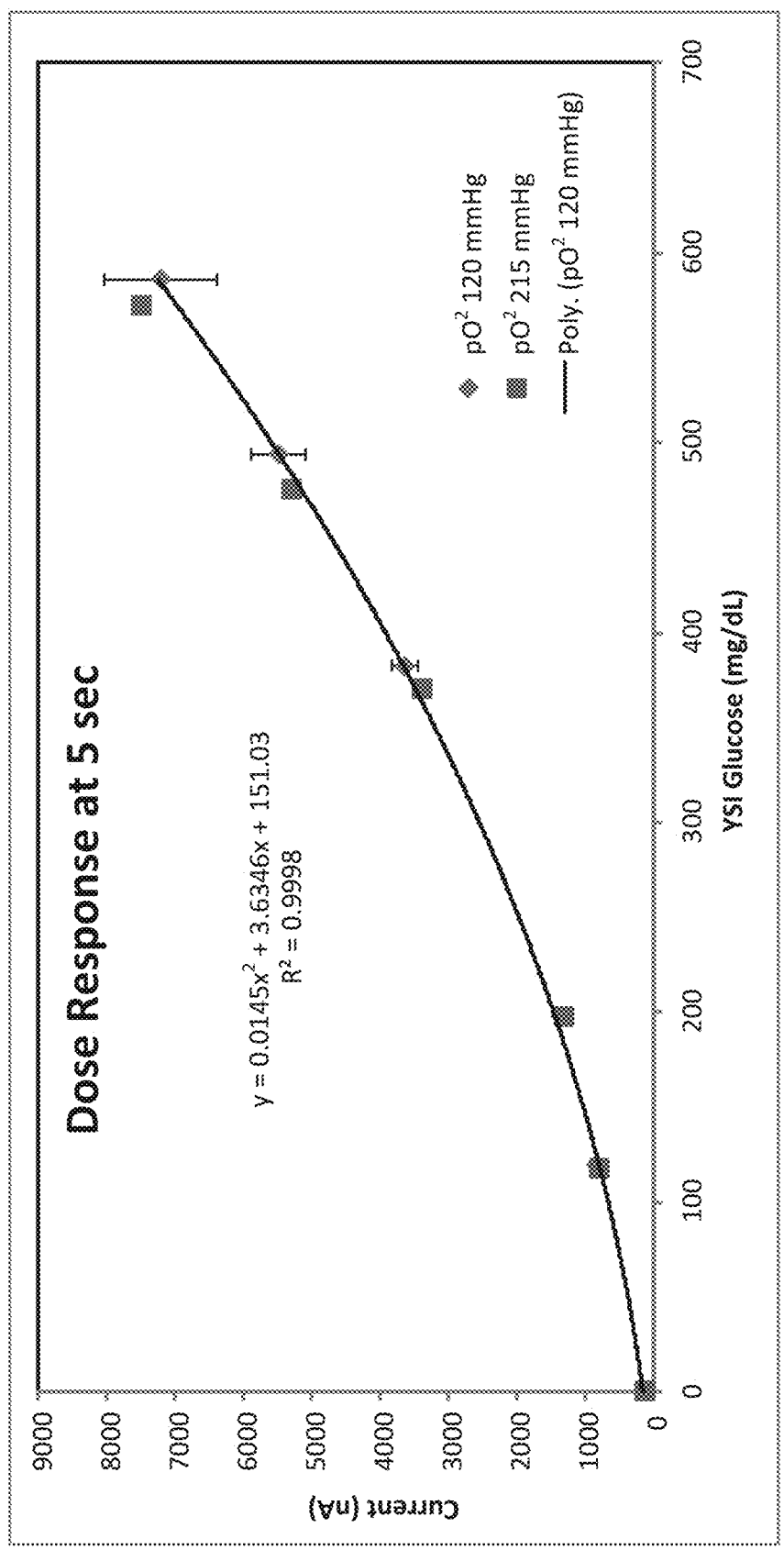
FIG. 5 is a dose response curve for reagent formulation comprising GOX and a multi-mediator formulation comprising 150 mM of Ru(NH$_3$)$_6$Cl$_3$ and 5 mM of [Os(III)(bpy)$_2$imCl]Cl$_2$ at pO$_2$ values of 120 mm Hg and 215 mm Hg.

Furthermore, FIG. 5 shows that the dose response curves of the mediator formulation (150 mM $Ru(NH_3)_6Cl_3$ and 5 mM $[Os(III)(bpy)_2imCl]Cl_2$) with GOX overlap at different $pO_2$ values (120 and 215 mm Hg), demonstrating negligible $O_2$ interference. The dose response of this mediator formulation with GOX is comparable to the analogous system with FAD-GDH (see FIG. 7), which is oxygen insensitive. Accordingly, the multiple mediator formulation provides a synergistic benefit to minimize oxygen interference and measurement bias when used with GOX and GDH.

In accordance with the exemplary embodiments, the present disclosure provides, inter alia, a mediator formulation comprising at least one osmium compound and at least one ruthenium compound. The present disclosure further provides, inter alia, a reagent formulation comprising said mediator formulation, and an oxidoreductase optionally comprising a cofactor and/or coenzyme. The reagent formulation may optionally further comprise additional excipients such as, for example, wetting agents binding agents, thickening agents, stabilizing agents, and buffering agents.

As described herein, the mediator formulations and reagent formulations of the present disclosure may be used in an electrochemical sensor for measuring the analyte level in a sample. The sensor may further comprises a test strip and a meter. The test strip comprises a working electrode and a counter electrode, with at least one of the electrodes being partially covered by the reagent formulation to form a reagent layer, wherein said reagent layer comprises an oxidoreductase optionally comprising a coenzyme and/or cofactor, and a mediator formulation as disclosed herein. Mediator formulations, reagent formulations, and/or reagent layers of the present disclosure may provide for improvements in accuracy, sensitivity, range of analysis, and stability.

In some embodiments, the reagent layer comprises an oxidoreductase comprising a coenzyme, which is FAD-GDH. In other embodiments, the reagent layer comprises NAD(P)-GDH. In other embodiments, the reagent layer comprises GOX. In addition, a mediator formulation comprising at least one osmium compound and at least one ruthenium compound may be incorporated into the reagent layer with the oxidoreductase. In a preferred embodiment, a compound of Formula I (e.g., [Os(III)(bpy)$_2$imCl]Cl$_2$) and a ruthenium compound (e.g., Ru(NH$_3$)$_6$Cl$_3$) are combined with FAD-GDH in the reagent layer. In another preferred embodiment, a compound of Formula I (e.g. [Os(III)(bpy)$_2$imCl]Cl$_2$) and a ruthenium compound (e.g., ruthenium hexaamine trichloride) are combined with NAD(P)-GDH in the reagent layer. In another preferred embodiment, a compound of Formula I (e.g. [Os(III)(bpy)$_2$imCl]Cl$_2$) and a ruthenium compound (e.g., Ru(NH$_3$)$_6$Cl$_3$) are combined with GOX in the reagent layer.

Other analyte/enzyme pairings are possible, and the present disclosure is not limited to glucose/FAD-GDH, NAD(P)-GDH, or glucose/GOX. Non-limiting examples of analytes include glucose, cholesterol, hemoglobin $A_{1C}$, fructose, alcohol, lactate, triglycerides, creatine, creatinine, bilirubin, uric acid, amino acids, ketones, coagulation factors, and the like. Non-limiting examples of enzymes include oxidoreductases such as, for example, glucose dehydrogenase, glucose oxidase, cholesterol oxidase, cholesterol esterase, bilirubin oxidase, fructosyl amino acid oxidase, fructosyl peptide oxidase, neutral proteinase, lactate dehydrogenase, lactate oxidase, pyruvate oxidase, alcohol dehydrogenase, lipoprotein lipase, glyceral kinase, alcohol oxidase, uricase, and the like. The enzyme may optionally utilize a cofactor and/or coenzyme. Non-limiting examples of coenzymes and cofactors include flavin nucleoside derivatives (e.g., FAD, FADH$_2$, FMN, FMNH$_2$, and the like), nicotinamide nucleotide derivatives (e.g., NAD(P), NAD. NADH/H$^+$, NADP, NADPH/H$_2$, and the like), and ubiquinones (e.g., Q, PQQ, and the like). Non-limiting examples of enzyme/cofactor or enzyme/coenzyme pairings include flavin adenine dinucleotide-dependent glucose dehydrogenase (FAD-GDH), nicotinamide adenine dinucleotide(phosphate)-dependent glucose dehydrogenase (NAD(P)-GDH), pyrroloquinoline quinone-dependent glucose dehydrogenase (PQQ-GDH), and glucose oxidase (GOX), which comprises FAD in its core.

Optionally, the reagent formulation or reagent layer may include inert ingredients that are not directly involved in any oxidation-reduction reactions in the electrochemical sensor. Examples of such inert ingredients include, but are not limited to, wetting agents, binding agents, thickening agents, stabilizers, and buffering components. Binding agents may include, but are not limited to, bentone, polyethylene oxide, and/or carbomethyl cellulose. Thickening agents may include, but are not limited to, silica, polyethylene oxide, and/or hydroxypropyl methylcellulose, polyethylene glycol polyvinyl alcohol, and the like. Buffering components may be made up of one or more, e.g., two, three, four or more, distinct buffering agents, where the buffering component stabilizes the mediator during storage of the composition in dry form such that little if any of the mediator is reduced prior to use, e.g., during storage. A buffer is considered to stabilize a mediator if, in the presence of the buffer, little if any of the mediator converts to a reduced form over a given storage period. Preferably, suitable buffers are buffers that do not cause the background signal in an electrochemical test to increase over time. The background signal is the signal obtained when analyte-free sample is introduced to the electrochemical testing system.

A suitable buffer or buffering agent may include, but are not limited to, any buffer which can be used in a conventional glucose sensor or a glucose sensor to be developed. Non-limiting examples of buffers may include acetate buffers, citrate buffers, and phosphate buffers. Buffers may also include, for example, those that are amine-based or contain a carboxyl group. Non-limiting examples of amine-based buffers include Tris (tris(hydroxymethyl)-aminomethane), ACES (N-(2-Acetamido)-2-aminoethanesulfonic acid), CHES (N-Cyclohexyl-2-aminoethanesulfonic acid), CAPSO, TAPS (N-Tris(hydroxymethyl)methyl-3-aminopropanesulfonic acid), CAPS (N-Cyclohexyl-3-aminopropanesulfonic acid), Bis-Tris (Bis(2-hydroxyethyl)iminotris (hydroxymethyl)methane), TAPSO (2-Hydroxy-N-tris(hydroxymethyl)methyl-3-aminopropanesulfonic), TES (N-Tris(hydroxymethyl)methyl-2-aminoethanesulfonic acid), Tricine, and ADA (N-(2-Acetamido)iminodiacetic acid). Non-limiting examples of buffers containing a carboxyl group include sodium and potassium acetate, sodium carbonate and bicarbonate, and potassium carbonate and bicarbonate. Non-limiting examples of phosphate buffers include potassium phosphates (potassium dihydrogen phosphate, potassium hydrogen phosphate, and tripotassium phosphate) and sodium phosphates (sodium dihydrogen phosphate, sodium hydrogen phosphate, and trisodium phosphate). Preferably, the buffer is a phosphate buffer. Any of these buffers may be used alone or in combination with each other.

A wetting agent may be added to facilitate uniform coating of the reagent composition onto an electrochemical test strip. A wetting agent may be used in combination with a detergent A plurality of one or more of the combination of wetting agents may also be used. The wetting agents used may improve dissolution of the assay reagents as well as enhance the wicking properties of a capillary fill strip. The wetting agents include those known in the art, for example, polymers, anti-foaming agents, and surfactants. Surfactants may include, but are not limited to, nonionic, anionic, cationic, and ampholytic surfactants and can be used alone or in combinations. Non-limiting examples of surfactants/detergents of interest also include: Tritons, Macols, Tetronics, Silwets, Zonyls, and Pluronics. Suitable agents include Triton materials which include, but are not limited to, Triton X Series (e.g. Triton X-100), Triton BG-10, Triton CF Surfactants, Triton DF Surfactants, and Triton CG Surfactants. Suitable agents also include Pluronic materials which are block co-polymers of polyethylene oxide and polypropylene oxide. Examples of Pluronic materials include, but are not limited to, Pluronic and Pluronic F87 Prill.

Some reagent compositions may also include one or more enzyme cofactors. Non-limiting examples of enzyme cofactors include divalent metal cations such as, for example, $Ca^{2+}$ and/or $Mg^{2+}$.

Stabilizers may also be added to the reagent composition to help stabilize the enzyme and prevent denaturation of the protein. The stabilizer may also help stabilize the redox state of the mediator, in particular, the oxidized redox mediator. Examples of stabilizing agents include, but are not limited to carbohydrates (e.g. sucrose, trehalose, mannitol, and lactose), amino acids, proteins (e.g. BSA and albumin) and organic compounds such as EDTA and the like.

In some embodiments, the present disclosure relates to an electrochemical sensor for measuring an analyte. The sensor may include a test strip and a meter. The test strip includes a reagent layer comprising at least one of the reagent compositions described herein. An individual test strip may also include an embedded code relating to data associated with multiple test strips, or data particular to that individual strip.

In some embodiments, the meter may be battery powered. In some aspects, when not in use, the meter may stay in a low-power sleep mode in order to save power. When the test strip is inserted into the meter, the first and second groups of electrical contacts on the test strip contact corresponding electrical contacts in the meter. The second group of electrical contacts may link a pair of electrical contacts in the meter, causing a current to flow through a portion of the second group of electrical contacts. The current flow through the second group of electrical contacts causes the meter to awaken and switch to an active mode. The meter also reads the code information provided by the second group of electrical contacts and can then identify, for example, the particular test to be performed, or a confirmation of proper operating status. In some aspects, based on the code information, the meter may also identify the inserted strip as either a test strip or a check strip based. If the meter recognizes a check strip, it performs a check strip sequence. If the meter recognizes a test strip, it performs a test strip sequence.

In some embodiments of the test strip sequence, the meter verifies the working electrode, counter electrode, and, if included, the fill-detect electrodes, by confirming that there are no low-impedance paths between any of these electrodes. If verified, the meter indicates that the sample may be applied to the test strip. The meter then applies a drop-detect voltage between the working and counter electrodes and detects a fluid sample, for example, a blood sample, by detecting a current flow between the working and counter electrodes (for example, a current flow through the blood sample as it links the working and counter electrodes). In some embodiments, the meter may apply a fill-detect voltage between the fill-detect electrodes and measure any resulting current flowing between the fill-detect electrodes to detect that sufficient sample is present and that the sample has mixed with the chemical and biological constituents in the reagent layer. If this resulting current reaches a sufficient level within a predetermined period of time, the meter indicates that sufficient sample is present and has mixed with the reagent layer.

In some embodiments, the meter can be programmed to wait for a predetermined period of time after initially detecting the blood sample, to allow the blood sample to react with the reagent layer. In some embodiments, the meter can immediately begin taking readings in sequence. While measuring a fluid sample, the meter applies an assay voltage between the working and counter electrodes and takes one or more measurements of the resulting current flowing between the working and counter electrodes. The assay voltage is near the redox potential of the formulation in the reagent layer, and the resulting current is related to the concentration of the particular analyte measured, such as, for example, the glucose level in a blood sample.

In some embodiments, any mediator formulation comprising at least one ruthenium compound and at least one osmium compound, reagent formulation, and/or reagent layer described herein, may react with glucose in the blood sample to measure the glucose concentration. In some embodiments, the reagent formulation and/or reagent layer comprises FAD-GDH, which reacts with glucose in the blood sample to measure the glucose concentration. The recitation of FAD-GDH is intended as an example only and other oxidoreductases (e.g., GOX) can be used without departing from the scope of the present disclosure. When exposed to a blood sample, FAD-GDH initiates a reaction that oxidizes the glucose to gluconic acid and reduces the mediator combination. When an appropriate voltage is applied to a working electrode, relative to a counter electrode, the reduced mediator combination generates a current relating to the glucose concentration in the blood sample. The meter then determines the glucose level based on the measured current and on calibration data that the meter has been signaled to access by the code data read from the second plurality of electrical contacts associated with the test strip. The meter then displays the calculated glucose level to the user.

In some embodiments, any mediator formulation comprising at least one ruthenium compound and at least one osmium compound, reagent formulation, or reagent layer described herein, may be used in a continuous analyte monitoring system for monitoring an analyte, such as, for example, glucose. In some aspects, the continuous analyte system may be configured to detect one or more analyte levels, such as, for example, glucose.

In some aspects, the continuous analyte monitoring system may comprise:
at least one sensor configured to detect one or more analyte levels;
at least one transmitter, wherein the transmitter is coupled to the sensor to detect one or more analyte levels, and wherein the transmitter periodically transmits signals corresponding to one or more detected analyte levels; and
at least one receiver, wherein the receiver is coupled to the transmitter to receive the transmitted signals corresponding to one or more detected analyte levels.

In some aspects, the continuous analyte monitoring system is a continuous glucose monitoring system and may comprise:
at least one sensor configured to detect one or more glucose levels;
at least one transmitter, wherein the transmitter is coupled to the sensor to detect one or more glucose levels, and wherein the transmitter periodically transmits signals corresponding to one or more detected glucose levels; and
at least one receiver, wherein the received is coupled to the transmitter to receive the transmitted signals corresponding to one or more detected glucose levels.

In some aspects, the continuous analyte sensor may be configured to produce a data signal indicative of an analyte concentration in a host during exposure of the sensor to a biological sample. In some aspects, the continuous analyte sensor is implanted in a host, for example, under the skin, for continuous in-vivo monitoring. In some aspects, the continuous analyte sensor continuously detects one or more analyte levels in-vivo and transfers the detected analyte level information at predetermined time intervals to data processing devices for monitoring, diagnosis, and/or analysis.

EXEMPLARY EMBODIMENTS

Each aspect, embodiment or feature described herein may be combined with any other aspect(s), embodiment(s) or feature(s) unless clearly indicated to the contrary.

In some embodiments, the present disclosure provides a mediator formulation comprising:
  at least one osmium compound; and
  at least one ruthenium compound.

In some embodiments, the present disclosure provides a mediator formulation comprising:
  at least one osmium compound; and
  at least one ruthenium compound;
  wherein the osmium compound is present in a concentration from about 1 mM to about 50 mM, preferably from about 1 mM to about 10 mM, and most preferably about 5 mM;
  and wherein the ruthenium compound is present in a concentration from about 100 mM to about 200 mM, preferably about 150 mM.

In some embodiments, the present disclosure provides a mediator formulation comprising:
  at least one compound of Formula I:

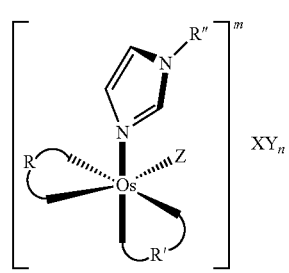

Formula I wherein:
  R and R' are the same or different and are selected from 2,2'-bipyridyl, 4,4'-disubstituted-2,2'-bipyridyl, 5,5'-disubstituted-2,2'-bipyridyl, 1,10-phenanthrolinyl, 4,7-disubstituted-1,10-phenanthrolinyl, and 5,6-disubstituted-1,10-phenanthrolinyl, wherein the disubstitution is a methyl, ethyl, or phenyl group;
  R and R' are coordinated to Os at their nitrogen atoms;
  R" is selected from hydrogen, methyl, and ethyl;
  Z is chloro or bromo;
  m is +1 or +2;
  X is an anion selected from chloride, bromide, iodide, fluoride, tetrafluoroborate, perchlorate, nitrate, sulfate, carbonate, and sulfite;
  Y is an anion selected from chloride, bromide, iodide, fluoride, tetrafluoroborate, perchlorate, and nitrate;
  n is 1 or 0;
  with the proviso that if X is sulfate, carbonate, or sulfite, then n is 0;
  and with the proviso that if m is +1 then n is 0, and X is not sulfate, carbonate, or sulfite;
  and wherein the aqueous solubility of the compound is greater than about 1 mM; and
  at least one ruthenium compound.

In some embodiments, the present disclosure provides a mediator formulation comprising:
  at least one compound of Formula I; and
  at least one ruthenium compound;
  wherein the compound of Formula I is present in a concentration from about 1 mM to about 50 mM, preferably from about 1 mM to about 10 mM, and most preferably about 5 mM;
  and wherein the ruthenium compound is present in a concentration from about 100 mM to about 200 mM, preferably about 150 mM.

In some embodiments, the present disclosure provides a mediator formulation comprising:
  at least one compound of Formula I; and
  ruthenium hexammine trichloride ($Ru(NH_3)_6Cl_3$).

In some embodiments, the present disclosure provides a mediator formulation comprising:
  at least one compound of Formula I; and
  ruthenium hexammine trichloride ($Ru(NH_3)_6Cl_3$);
  wherein the compound of Formula I is present in a concentration from about 1 mM to about 50 mM, preferably from about 1 mM to about 10 mM, and most preferably about 5 mM;
  and wherein $Ru(NH_3)_6Cl_3$ is present in a concentration from about 100 mM to about 200 mM, preferably about 150 mM.

In some embodiments, the multiple mediator formulation comprises $[Os(III)(bpy)_2imCl]Cl_2$ and ruthenium hexammine trichloride ($Ru(NH_3)_6Cl_3$).

In some embodiments, the multiple mediator formulation comprises $[Os(III)(bpy)_2imCl]Cl_2$ and ruthenium hexammine trichloride ($Ru(NH_3)_6Cl_3$);
  wherein $[Os(III)(bpy)_2imCl]Cl_2$ is present in a concentration from about 1 mM to about 50 mM, preferably from about 1 mM to about 10 mM, and most preferably about 5 mM;
  and wherein $Ru(NH_3)_6Cl_3$ is present in a concentration from about 100 mM to about 200 mM, preferably about 150 mM.

In some embodiments, the mediator formulation comprises about 5 mM $[Os(III)(bpy)_2imCl]Cl_2$ and about 150 mM $Ru(NH_3)_6Cl_3$.

In some embodiments, the present disclosure provides a reagent formulation comprising:
  an oxidoreductase optionally comprising a coenzyme and/or cofactor; and
  any mediator formulation as described herein.

In some embodiments, the present disclosure provides a reagent formulation comprising:
  a mediator formulation comprising at least one osmium compound and at least one ruthenium compound; and
  an oxidoreductase optionally comprising a coenzyme and/or cofactor.

In some embodiments, the osmium compound is a compound of Formula I (such as, for example, $[Os(III)(bpy)_2imCl]Cl_2$). In some embodiments, the ruthenium compound is a ruthenium hexammine complex (such as, for example, $Ru(NH_3)_6Cl_3$). In some embodiments, the mediator formulation comprises $[Os(III)(bpy)_2imCl]Cl_2$ and $Ru(NH_3)_6Cl_3$. In some embodiments, the oxidoreductase optionally comprising a coenzyme and/or cofactor is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase. In some embodiments, the coenzyme is present and is a flavin nucleoside coenzyme. In some embodiments, the coenzyme is FAD. In some embodiments, the oxidoreductase optionally comprising a coenzyme and/or cofactor is FAD-GDH. In some embodiments, the oxidoreductase optionally comprising a coenzyme and/or cofactor is GOX.

In some embodiments, the present disclosure provides a reagent formulation comprising:
a mediator formulation comprising at least one osmium compound and at least one ruthenium compound; and
a glucose oxidoreductase optionally comprising a flavin nucleoside and/or a nicotinamide nucleotide coenzyme.

In some embodiments, the osmium compound is a compound of Formula I (such as, for example, [Os(III)(bpy)$_2$imCl]Cl$_2$). In some embodiments, the ruthenium compound is a ruthenium hexammine complex (such as, for example, Ru(NH$_3$)$_6$Cl$_3$). In some embodiments, the mediator formulation comprises [Os(III)(bpy)$_2$imCl]Cl$_2$ and Ru(NH$_3$)$_6$Cl$_3$. In some embodiments, the coenzyme is present and is a flavin nucleoside coenzyme. In some embodiments, the coenzyme is FAD. In some embodiments, the oxidoreductase is FAD-GDH. In some embodiments, the oxidoreductase is GOX.

In some embodiments, the reagent formulation comprises:
a mediator formulation comprising at least one compound of Formula I and at least one ruthenium compound; and
a glucose oxidoreductase optionally comprising a flavin nucleoside and/or a nicotinamide nucleotide coenzyme.

In some embodiments, the osmium compound is a compound of Formula I (such as, for example, [Os(III)(bpy)$_2$imCl]Cl$_2$). In some embodiments, the ruthenium compound is a ruthenium hexammine complex (such as, for example, Ru(NH$_3$)$_6$Cl$_3$). In some embodiments, the mediator formulation comprises [Os(III)(bpy)$_2$imCl]Cl$_2$ and Ru(NH$_3$)$_6$Cl$_3$. In some embodiments, the coenzyme is present and is a flavin nucleoside coenzyme. In some embodiments, the coenzyme is FAD. In some embodiments, the oxidoreductase is FAD-GDH. In some embodiments, the oxidoreductase is GOX.

In some embodiments, the reagent formulation comprises:
a mediator formulation comprising at least one compound of Formula I and ruthenium hexammine trichloride; and
a glucose oxidoreductase optionally comprising a flavin nucleoside and/or a nicotinamide nucleotide coenzyme.

In some embodiments, the osmium compound is a compound of Formula I (such as, for example, [Os(III)(bpy)$_2$imCl]Cl$_2$). In some embodiments, the ruthenium compound is a ruthenium hexammine complex (such as, for example, Ru(NH$_3$)$_6$Cl$_3$). In some embodiments, the mediator formulation comprises [Os(III)(bpy)$_2$imCl]Cl$_2$ and Ru(NH$_3$)$_6$Cl$_3$. In some embodiments, the coenzyme is present and is a flavin nucleoside coenzyme. In some embodiments, the coenzyme is FAD. In some embodiments, the oxidoreductase is FAD-GDH. In some embodiments, the oxidoreductase is GOX.

In some embodiments, the reagent formulation comprises:
a mediator formulation comprising [Os(III)(bpy)$_2$imCl]Cl$_2$ and ruthenium hexammine trichloride (Ru(NH$_3$)$_6$Cl$_3$); and
a glucose oxidoreductase optionally comprising a flavin nucleoside and/or a nicotinamide nucleotide coenzyme.

In some embodiments, the coenzyme is present and is a flavin nucleoside coenzyme. In some embodiments, the coenzyme is FAD. In some embodiments, the oxidoreductase is FAD-GDH. In some embodiments, the oxidoreductase is GOX.

In some embodiments, the reagent formulation comprises:
a mediator formulation comprising [Os(III)(bpy)$_2$imCl]Cl$_2$ and ruthenium hexammine trichloride (Ru(NH$_3$)$_6$Cl$_3$); and
an oxidoreductase optionally comprising a flavin nucleoside and/or a nicotinamide nucleotide coenzyme.

In some embodiments, the oxidoreductase is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase. In some embodiments, the coenzyme is present and is a flavin nucleoside coenzyme. In some embodiments, the coenzyme is FAD. In some embodiments, the oxidoreductase optionally comprising a coenzyme and/or cofactor is FAD-GDH. In some embodiments, the oxidoreductase optionally comprising a coenzyme and/or cofactor is GOX.

In some embodiments, the reagent formulation comprises a glucose oxidoreductase optionally comprising a flavin nucleoside and/or a nicotinamide nucleotide coenzyme, and a mediator formulation, wherein:
the glucose oxidoreductase is GDH;
the coenzyme, if present, is selected from FAD and NAD(P); and
the mediator formulation comprises at least one osmium compound and at least one ruthenium compound.

In some embodiments, the osmium compound is a compound of Formula I (such as, for example, [Os(III)(bpy)$_2$imCl]Cl$_2$). In some embodiments, the ruthenium compound is a ruthenium hexammine complex (such as, for example, Ru(NH$_3$)$_6$Cl$_3$). In some embodiments, the mediator formulation comprises [Os(III)(bpy)$_2$imCl]Cl$_2$ and Ru(NH$_3$)$_6$Cl$_3$. In some embodiments, the coenzyme is FAD.

In some embodiments, the reagent formulation comprises a glucose oxidoreductase optionally comprising a flavin nucleoside and/or a nicotinamide nucleotide coenzyme, and a mediator formulation, wherein:
the glucose oxidoreductase is GDH;
the coenzyme, if present, is FAD; and
the mediator formulation comprises at least one osmium compound and at least one ruthenium compound.

In some embodiments, the osmium compound is a compound of Formula I (such as, for example, [Os(III)(bpy)$_2$imCl]Cl$_2$). In some embodiments, the ruthenium compound is a ruthenium hexammine complex (such as, for example, Ru(NH$_3$)$_6$Cl$_3$). In some embodiments, the mediator formulation comprises [Os(III)(bpy)$_2$imCl]Cl$_2$ and Ru(NH$_3$)$_6$Cl$_3$.

In some embodiments, the reagent formulation comprises a glucose oxidoreductase optionally comprising a flavin nucleoside and/or a nicotinamide nucleotide coenzyme, and a mediator formulation, wherein:
the glucose oxidoreductase is GDH;
the coenzyme, if present, is FAD; and
the mediator formulation comprises at least one compound of Formula I and at least one ruthenium compound.

In some embodiments, the compound of Formula I is [Os(III)(bpy)$_2$imCl]Cl$_2$. In some embodiments, the ruthenium compound is a ruthenium hexammine complex (such as, for example, Ru(NH$_3$)$_6$Cl$_3$). In some embodiments, the mediator formulation comprises [Os(III)(bpy)$_2$imCl]Cl$_2$ and Ru(NH$_3$)$_6$Cl$_3$.

In some embodiments, the reagent formulation comprises a glucose oxidoreductase optionally comprising a flavin nucleoside and/or a nicotinamide nucleotide coenzyme, and a mediator formulation, wherein:
  the glucose oxidoreductase is GDH;
  the coenzyme, if present, is FAD; and
  the mediator formulation comprises at least one compound of Formula I and ruthenium hexammine trichloride.

In some embodiments, the compound of Formula I is [Os(III)(bpy)$_2$imCl]Cl$_2$. In some embodiments, the mediator formulation comprises [Os(III)(bpy)$_2$imCl]Cl$_2$ and Ru(NH$_3$)$_6$Cl$_3$.

In some embodiments, the reagent formulation comprises a glucose oxidoreductase optionally comprising a flavin nucleoside and/or a nicotinamide nucleotide coenzyme, and a mediator formulation, wherein:
  the glucose oxidoreductase is GDH;
  the coenzyme, if present, is FAD; and
  the mediator formulation comprises [Os(III)(bpy)$_2$imCl] Cl$_2$ and ruthenium hexammine trichloride (Ru(NH$_3$)$_6$Cl$_3$).

In some embodiments, the reagent formulation comprises a glucose oxidoreductase, an optional flavin nucleoside and/or a nicotinamide nucleotide coenzyme, and a mediator formulation, wherein:
  the glucose oxidoreductase is GOX;
  the coenzyme, if present, is FAD; and
  the mediator formulation comprises at least one osmium compound and at least one ruthenium compound.

In some embodiments, the osmium compound is a compound of Formula I (such as, for example, [Os(III)(bpy)$_2$imCl]Cl$_2$). In some embodiments, the ruthenium compound is a ruthenium hexammine complex (such as, for example, Ru(NH$_3$)$_6$Cl$_3$). In some embodiments, the mediator formulation comprises [Os(III)(bpy)$_2$imCl]Cl$_2$ and Ru(NH$_3$)$_6$Cl$_3$.

In some embodiments, the reagent formulation comprises a glucose oxidoreductase optionally comprising a flavin nucleoside and/or a nicotinamide nucleotide coenzyme, and a mediator formulation, wherein:
  the glucose oxidoreductase is GOX;
  the coenzyme, if present, is FAD; and
  the mediator formulation comprises at least one compound of Formula I and at least one ruthenium compound.

In some embodiments, the compound of Formula I is [Os(III)(bpy)$_2$imCl]Cl$_2$. In some embodiments, the ruthenium compound is a ruthenium hexammine complex (such as, for example, Ru(NH$_3$)$_6$Cl$_3$). In some embodiments, the mediator formulation comprises [Os(III)(bpy)$_2$imCl]Cl$_2$ and ruthenium hexammine trichloride (Ru(NH$_3$)$_6$Cl$_3$).

In some embodiments, the reagent formulation comprises a glucose oxidoreductase optionally comprising a flavin nucleoside and/or a nicotinamide nucleotide coenzyme, and a mediator formulation, wherein:
  the glucose oxidoreductase is GOX;
  the coenzyme, if present, is FAD; and
  the mediator formulation comprises at least one compound of Formula I and ruthenium hexammine trichloride (Ru(NH$_3$)$_6$Cl$_3$).

In some embodiments, the compound of Formula I is [Os(III)(bpy)$_2$imCl]Cl$_2$. In some embodiments, the mediator formulation comprises [Os(III)(bpy)$_2$imCl]Cl$_2$ and ruthenium hexammine trichloride.

In some embodiments, the reagent formulation comprises a glucose oxidoreductase optionally comprising a flavin nucleoside coenzyme and/or a nicotinamide nucleotide coenzyme, and a mediator formulation, wherein:
  the glucose oxidoreductase is GOX;
  the coenzyme, if present, is FAD; and
  the mediator formulation comprises [Os(III)(bpy)$_2$imCl]Cl$_2$ and ruthenium hexammine trichloride (Ru(NH$_3$)$_6$Cl$_3$).

In some embodiments, the reagent formulation of any of the embodiments herein further comprises at least one buffer, at least one thickening agent, and at least one surfactant.

In some embodiments, the reagent formulation of any of the embodiments herein further comprises at least one buffer, at least one thickening agent, and at least one surfactant, wherein:
  the at least one buffer is phosphate buffer;
  the at least one thickening agent is hydroxypropyl methylcellulose; and
  the at least one surfactant is Triton X-100.

In some embodiments, the reagent formulation of any of the embodiments herein is at a pH in the range of about 2.0 to about 11.0.

In some embodiment, the reagent formulation of any of the embodiments herein is at a pH in the range of about 5.7 to about 8.0.

In some embodiments, the reagent formulation of any of the embodiments herein is at a pH in the range of about 6.0 to about 7.0.

In some preferred embodiments, the reagent formulation of any of the embodiments herein is at a pH of about 6.3.

In some embodiments, the at least one osmium compound, compound of Formula I, or [Os(III)(bpy)$_2$imCl]Cl$_2$ of any of the embodiments herein is present in a range of about 1 to about 50 mM.

In some embodiments, the at least one osmium compound, compound of Formula I, or [Os(III)(bpy)$_2$imCl]Cl$_2$ of any of the embodiments herein is present in a range of about 1 to about 25 mM.

In some embodiments, the at least one osmium compound, compound of Formula I, or [Os(III)(bpy)$_2$imCl]Cl$_2$ of any of the embodiments herein is present in a range of about 1 to about 10 mM.

In some embodiments, the at least one osmium compound, compound of Formula I, or [Os(III)(bpy)$_2$imCl]Cl$_2$ of any of the embodiments herein is present in a range of about 5 mM to about 10 mM.

In some embodiments, the at least one osmium compound, compound of Formula I, or [Os(III)(bpy)$_2$imCl]Cl$_2$ of any of the embodiments herein, is present in a concentration of about 1 mM, about 2 mM, about 5 mM, or about 10 mM.

In some preferred embodiments, the at least one osmium compound, compound of Formula I, or [Os(III)(bpy)$_2$imCl]Cl$_2$ of any of the embodiments herein, is present in a concentration of about 5 mM.

In some embodiments, the at least one ruthenium compound or the ruthenium hexammine trichloride (Ru(NH$_3$)$_6$Cl$_3$) of any of the embodiments herein, is present in a range of about 100 to about 200 mM.

In some embodiments, the at least one ruthenium compound or the ruthenium hexammine trichloride (Ru(NH$_3$)$_6$Cl$_3$) of any of the embodiments herein, is present in a range of about 125 mM to about 175 mM.

In some embodiments, the at least one ruthenium compound or the ruthenium hexammine trichloride (Ru(NH$_3$)$_6$Cl$_3$) of any of the embodiments herein, is present in a concentration of about 100 mM, about 125 mM, about 150 mM, about 175 mM, or about 200 mM.

In some preferred embodiments, the at least one ruthenium compound or the ruthenium hexammine trichloride ($Ru(NH_3)_6Cl_3$) of any of the embodiments herein, is present in a concentration of about 150 mM.

In some embodiments, the at least one buffer or the phosphate buffer of any of the embodiments herein is present in a range of about 10 mM to about 250 mM.

In some embodiments, the at least one buffer or the phosphate buffer of any of the embodiments herein is present in a range of about 25 mM to about 75 mM.

In some preferred embodiments, the at least one buffer or the phosphate buffer of any of the embodiments herein is present in a concentration of about 50 mM.

In some embodiments, the at least one surfactant or Triton X-100 of any of the embodiments herein is present in a range of about 0% v/v to about 1% v/v.

In some embodiments, the at least one surfactant or Triton X-100 of any of the embodiments herein is present in a range of about 0% v/v to about 0.5% v/v.

In some embodiments, the at least one surfactant or Triton X-100 of any of the embodiments herein is present in a range of about 0% v/v to about 0.1% v/v.

In some preferred embodiments, the at least one surfactant or Triton X-100 of any of the embodiments herein is present in a concentration of about 0.06% v/v.

In some embodiments, the at least one thickening agent or hydroxypropyl methylcellulose of any of the embodiments herein is present in a concentration of about 0% w/v to about 5% w/v.

In some embodiments, the at least one thickening agent or hydroxypropyl methylcellulose of any of the embodiments herein is present in a concentration of about 0% w/v to about 1% w/v.

In a preferred embodiment, the at least one thickening agent or hydroxypropyl methylcellulose of any of the embodiments herein is present in a concentration of about 0.25% w/v.

In some embodiments, the oxidoreductase, glucose oxidoreductase, GOX, GDH, FAD-GDH or NAD(P)-GDH of any of the embodiments herein is present in a range of about 1,000 to about 25,000 U/mL.

In some embodiments, the oxidoreductase, glucose oxidoreductase, GOX, GDH, FAD-GDH or NAD(P)-GDH of any of the embodiments herein is present in a range of about 5,000 to about 15,000 U/mL.

In some embodiments, the oxidoreductase, glucose oxidoreductase, GOX, GDH, FAD-GDH or NAD(P)-GDH of any of the embodiments herein is present in a range of about 8,000 U/mL to about 12,000 U/mL.

In some preferred embodiments, the oxidoreductase, glucose oxidoreductase, GOX, FAD-GDH or NAD(P)-GDH of any of the embodiments herein is present in a concentration of about 10,000 U/mL.

In some embodiments, the reagent formulation comprises:
(i) about 10 mM to about 250 mM buffer;
(ii) about 1,000 U/mL to about 25,000 U/mL oxidoreductase optionally comprising a coenzyme and/or cofactor;
(iii) about 100 mM to about 200 mM $Ru(NH_3)_6Cl_3$;
(iv) about 1 mM to about 50 mM $[Os(III)(bpy)_2imCl]Cl_2$;
(v) about 0% w/v to about 5% w/v thickening agent; and
(vi) about 0% v/v to about 1% v/v surfactant;
wherein the pH of the reagent formulation is in the range of about 2.0 to about 11.0.
In some embodiments, the oxidoreductase is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase. In some embodiments, the oxidoreductase comprises a flavin nucleoside and/or a nicotinamide nucleotide coenzyme. In some embodiments, the coenzyme is flavin adenine dinucleotide (FAD).

In some embodiments, the reagent formulation comprises:
(i) about 10 mM to about 250 mM buffer;
(ii) about 1,000 U/mL to about 25,000 U/mL glucose oxidoreductase optionally comprising a coenzyme and/or cofactor;
(iii) about 100 mM to about 200 mM $Ru(NH_3)_6Cl_3$;
(iv) about 1 mM to about 50 mM $[Os(III)(bpy)_2imCl]Cl_2$;
(v) about 0% w/v to about 5% w/v thickening agent; and
(vi) about 0% v/v to about 1% v/v surfactant;
wherein the pH of the reagent formulation is in the range of about 2.0 to about 11.0.
In some embodiments, the glucose oxidoreductase optionally comprising a coenzyme and/or cofactor is selected from GOX, FAD-GDH or NAD(P)-GDH. In some embodiments, the glucose oxidoreductase optionally comprising a coenzyme and/or cofactor is FAD-GDH. In some embodiments, the glucose oxidoreductase optionally comprising a coenzyme and/or cofactor is GOX.

In some embodiments, the reagent formulation comprises:
(i) about 10 mM to about 250 mM phosphate buffer;
(ii) about 1,000 U/mL to about 25,000 U/mL FAD-GDH;
(iii) about 100 mM to about 200 mM $Ru(NH_3)_6Cl_3$;
(iv) about 1 mM to about 50 mM, $[Os(III)(bpy)_2imCl]Cl_2$;
(v) about 0% w/v to about 5% w/v hydroxypropyl methylcellulose; and
(vi) about 0% v/v to about 1% v/v Triton X-100;
wherein the pH of the reagent formulation is in the range of about 2.0 to about 11.0.

In some embodiments, the reagent formulation comprises:
(i) about 10 mM to about 250 mM phosphate buffer;
(ii) about 1,000 U/mL to about 25,000 U/mL GOX;
(iii) about 100 mM to about 200 mM $Ru(NH_3)_6Cl_3$;
(iv) about 1 mM to about 50 mM, $[Os(III)(bpy)_2imCl]Cl_2$;
(v) about 0% w/v to about 5% w/v hydroxypropyl methylcellulose; and
(vi) about 0% v/v to about 1% v/v Triton X-100;
wherein the pH of the reagent formulation is in the range of about 2.0 to about 11.0.

In some embodiments, the reagent formulation comprises:
(i) about 10 mM to about 250 mM buffer;
(ii) about 10,000 U/mL oxidoreductase optionally comprising a coenzyme and/or cofactor;
(iii) about 150 mM $Ru(NH_3)_6Cl_3$;
(iv) about 1 mM to about 10 mM $[Os(III)(bpy)_2imCl]Cl_2$;
(v) about 0% w/v to about 1% w/v thickening agent; and
(vi) about 0% v/v to about 0.5% v/v surfactant;
wherein the pH of the reagent formulation is in the range of about 5.7 to about 8.0.
In some embodiments, the oxidoreductase is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase. In some embodiments, the oxidoreductase further comprises a flavin nucleoside and/or a nicotinamide nucleotide coenzyme. In some embodiments, the coenzyme is flavin adenine dinucleotide (FAD).

In some embodiments, the reagent formulation comprises:
(i) about 10 mM to about 250 mM buffer;
(ii) about 10,000 U/mL glucose oxidoreductase optionally comprising a coenzyme and/or cofactor;
(iii) about 150 mM Ru(NH$_3$)$_6$Cl$_3$;
(iv) about 1 mM to about 10 mM [Os(III)(bpy)$_2$imCl]Cl$_2$;
(v) about 0% w/v to about 1% w/v thickening agent; and
(vi) about 0% v/v to about 0.5% v/v surfactant;
wherein the pH of the reagent formulation is in the range of about 5.7 to about 8.0.

In some embodiments, the glucose oxidoreductase optionally comprising a coenzyme and/or cofactor is selected from GOX, FAD-GDH or NAD(P)-GDH. In some embodiments, the glucose oxidoreductase is FAD-GDH. In some embodiments, the glucose oxidoreductase is GOX.

In some embodiments, the reagent formulation comprises:
(i) about 10 mM to about 250 mM phosphate buffer;
(ii) about 10,000 U/mL FAD-GDH;
(iii) about 150 mM Ru(NH$_3$)$_6$Cl$_3$;
(iv) about 1 mM to about 10 mM [Os(III)(bpy)$_2$imCl]Cl$_2$;
(v) about 0% w/v to about 1% w/v hydroxypropyl methylcellulose; and
(vi) about 0% v/v to about 0.5% v/v Triton X-100;
wherein the pH of the reagent formulation is in the range of about 5.7 to about 8.0.

In some embodiments, the reagent formulation comprises:
(i) about 10 mM to about 250 mM phosphate buffer;
(ii) about 10,000 U/mL FAD-GOX;
(iii) about 150 mM Ru(NH$_3$)$_6$Cl$_3$;
(iv) about 1 mM to about 10 mM [Os(III)(bpy)$_2$imCl]Cl$_2$;
(v) about 0% w/v to about 1% w/v hydroxypropyl methylcellulose; and
(vi) about 0% v/v to about 0.5% v/v Triton X-100;
wherein the pH of the reagent formulation is in the range of about 5.7 to about 8.0.

In some embodiments, the reagent formulation comprises:
(i) about 50 mM buffer;
(ii) about 10,000 U/mL oxidoreductase;
(iii) about 150 mM Ru(NH$_3$)$_6$Cl$_3$
(iv) about 1 mM to about 10 mM [Os(III)(bpy)$_2$imCl]Cl$_2$;
(v) about 0.25% w/v thickening agent; and
(vi) about 0.06% v/v surfactant;
wherein the pH of the reagent formulation is in the range of about 6.0 to about 7.0.

In some embodiments, the oxidoreductase is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase. In some embodiments, the oxidoreductase further comprises a flavin nucleoside and/or a nicotinamide nucleotide coenzyme. In some embodiments, the coenzyme is flavin adenine dinucleotide (FAD).

In some embodiments, the reagent formulation comprises:
(i) about 50 mM buffer;
(ii) about 10,000 U/mL glucose oxidoreductase;
(iii) about 150 mM Ru(NH$_3$)$_6$Cl$_3$;
(iv) about 1 mM to about 10 mM [Os(III)(bpy)$_2$imCl]Cl$_2$;
(v) about 0.25% w/v thickening agent; and
(vi) about 0.06% v/v surfactant;
wherein the pH of the reagent formulation is in the range of about 6.0 to about 7.0.

In some embodiments, the glucose oxidoreductase is selected from GDH, GOX, FAD-GDH, FAD-GOX, and NAD(P)-GDH. In some embodiments, the glucose oxidoreductase is FAD-GDH. In some embodiments, the glucose oxidoreductase is FAD-GOX.

In some embodiments, the reagent formulation comprises:
(i) about 50 mM phosphate buffer;
(ii) about 10,000 U/mL FAD-GDH;
(iii) about 150 mM Ru(NH$_3$)$_6$Cl$_3$;
(iv) about 1 mM to about 10 mM [Os(III)(bpy)$_2$imCl]Cl$_2$;
(v) about 0.25% w/v hydroxypropyl methylcellulose; and
(vi) about 0.06% v/v Triton X-100;
wherein the pH of the reagent formulation is in the range of about 6.0 to about 7.0.

In some embodiments, the reagent formulation comprises:
(i) about 50 mM phosphate buffer;
(ii) about 10,000 U/mL FAD-GOX;
(iii) about 150 mM Ru(NH$_3$)$_6$Cl$_3$;
(iv) about 1 mM to about 10 mM [Os(III)(bpy)$_2$imCl]Cl$_2$;
(v) about 0.25% w/v hydroxypropyl methylcellulose; and
(vi) about 0.06% v/v Triton X-100;
wherein the pH of the reagent formulation is in the range of about 6.0 to about 7.0.

In some embodiments, the reagent formulation comprises:
(i) about 50 mM buffer;
(ii) about 10,000 U/mL oxidoreductase optionally comprising a coenzyme and/or cofactor;
(iii) about 150 mM Ru(NH$_3$)$_6$Cl$_3$;
(iv) about 1 mM to about 10 mM [Os(III)(bpy)$_2$imCl]Cl$_2$;
(v) about 0.25% w/v thickening agent; and
(vi) about 0.06% v/v surfactant;
wherein the pH of the reagent formulation is about 6.3.

In some embodiments, the oxidoreductase is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase. In some embodiments, the oxidoreductase further comprises a flavin nucleoside and/or a nicotinamide nucleotide coenzyme. In some embodiments, the coenzyme is flavin adenine dinucleotide.

In some embodiments, the reagent formulation comprises:
(i) about 50 mM buffer;
(ii) about 10,000 U/mL glucose oxidoreductase optionally comprising a coenzyme and/or cofactor;
(iii) about 150 mM Ru(NH$_3$)$_6$Cl$_3$;
(iv) about 1 mM to about 10 mM [Os(III)(bpy)$_2$imCl]Cl$_2$;
(v) about 0.25% w/v thickening agent; and
(vi) about 0.06% v/v surfactant;
wherein the pH of the reagent formulation is about 6.3.

In some embodiments, the glucose oxidoreductase optionally comprising a coenzyme and/or cofactor is selected from GOX, FAD-GDH or NAD(P)-GDH. In some embodiments, the glucose oxidoreductase optionally comprising a coenzyme and/or cofactor is FAD-GDH. In some embodiments, the glucose oxidoreductase optionally comprising a coenzyme and/or cofactor is GOX.

In some embodiments, the reagent formulation comprises:
(i) about 50 mM phosphate buffer;
(ii) about 10,000 U/mL FAD-GDH;
(iii) about 150 mM Ru(NH$_3$)$_6$Cl$_3$;
(iv) about 1 mM to about 10 mM [Os(III)(bpy)$_2$imCl]Cl$_2$;
(v) about 0.25% w/v hydroxypropyl methylcellulose; and
(vi) about 0.06% v/v Triton X-100;
wherein the pH of the reagent formulation is about 6.3.

In some embodiments, the reagent formulation comprises:
(i) about 50 mM phosphate buffer;
(ii) about 10,000 U/mL FAD-GOX;
(iii) about 150 mM Ru(NH$_3$)$_6$Cl$_3$;

(iv) about 1 mM to about 10 mM [Os(III)(bpy)$_2$imCl]Cl$_2$;
(v) about 0.25% w/v hydroxypropyl methylcellulose; and
(vi) about 0.06% v/v Triton X-100;
wherein the pH of the reagent formulation is about 6.3.

In some embodiments, the reagent formulation comprises:
(i) about 50 mM buffer;
(ii) about 10,000 U/mL oxidoreductase optionally comprising a coenzyme and/or cofactor;
(iii) about 150 mM Ru(NH$_3$)$_6$Cl$_3$;
(iv) about 5 mM [Os(III)(bpy)$_2$imCl]Cl$_2$;
(v) about 0.25% w/v thickening agent; and
(vi) about 0.06% v/v surfactant;
wherein the pH of the reagent formulation is about 6.3.

In some embodiments, the oxidoreductase is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase. In some embodiments, the oxidoreductase further comprises a flavin nucleoside and/or a nicotinamide nucleotide coenzyme. In some embodiments, the coenzyme is flavin adenine dinucleotide.

In some embodiments, the reagent formulation comprises:
(i) about 50 mM buffer;
(ii) about 10,000 U/mL glucose oxidoreductase optionally comprising a coenzyme and/or cofactor;
(iii) about 150 mM Ru(NH$_3$)$_6$Cl$_3$;
(iv) about 5 mM [Os(III)(bpy)$_2$imCl]Cl$_2$;
(v) about 0.25% w/v thickening agent; and
(vi) about 0.06% v/v surfactant;
wherein the pH of the reagent formulation is about 6.3.

In some embodiments, the glucose oxidoreductase optionally comprising a coenzyme and/or cofactor is selected from GOX, FAD-GDH or NAD(P)-GDH. In some embodiments, the glucose oxidoreductase optionally comprising a coenzyme and/or cofactor is FAD-GDH. In some embodiments, the glucose oxidoreductase optionally comprising a coenzyme and/or cofactor is GOX.

In a preferred embodiment, the reagent formulation comprises:
(i) about 50 mM phosphate buffer;
(ii) about 10,000 U/mL FAD-GDH;
(iii) about 150 mM Ru(NH$_3$)$_6$Cl$_3$;
(iv) about 5 mM [Os(III)(bpy)$_2$imCl]Cl$_2$;
(v) about 0.25% w/v hydroxypropyl methylcellulose; and
(vi) about 0.06% v/v Triton X-100;
wherein the pH of the reagent formulation is about 6.3.

In a preferred embodiment, the reagent formulation comprises:
(i) about 50 mM phosphate buffer;
(ii) about 10,000 U/mL GOX;
(iii) about 150 mM Ru(NH$_3$)$_6$Cl$_3$;
(iv) about 5 mM [Os(III)(bpy)$_2$imCl]Cl$_2$;
(v) about 0.25% w/v hydroxypropyl methylcellulose; and
(vi) about 0.06% v/v Triton X-100;
wherein the pH of the reagent formulation is about 6.3.

In some embodiments, the reagent formulation according to any of the embodiments disclosed herein may further comprise at least one enzyme stabilizer.

In some embodiments, the reagent formulation may react with glucose in a blood sample in order to determine the particular glucose concentration, wherein the reagent formulation is according to any of the embodiments above.

In some embodiments, the reagent formulation may be used to form a reagent layer in a test strip, wherein the reagent formulation is according to any of the embodiments above.

Other embodiments of the invention will be apparent to those skilled in the art from consideration of the specification and practice of the invention disclosed herein. It is intended that the specification and examples be considered as exemplary only, with a true scope and spirit of the invention being indicated by the claims.

LIST OF EXEMPLARY EMBODIMENTS

Additional non-limiting exemplary embodiments are listed below:
1. A mediator formulation for detecting an analyte, comprising at least one osmium compound and at least one ruthenium compound.
2. The mediator formulation according to embodiment 1, wherein the at least one osmium compound is a compound of Formula I:

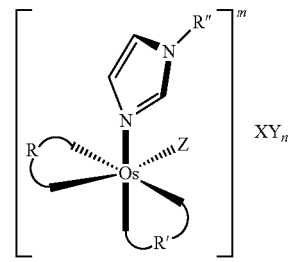

Formula I wherein:
R and R' are the same or different and are selected from 2,2'-bipyridyl, 4,4'-disubstituted-2,2'-bipyridyl, 5,5'-disubstituted-2,2'-bipyridyl, 1,10-phenanthrolinyl, 4,7-disubstituted-1,10-phenanthrolinyl, and 5,6-disubstituted-1,10-phenanthrolinyl, wherein the disubstitution is a methyl, ethyl, or phenyl group;
R and R' are coordinated to Os at their nitrogen atoms;
R" is selected from hydrogen, methyl, and ethyl;
Z is chloro or bromo;
m is +1 or +2;
X is an anion selected from chloride, bromide, iodide, fluoride, tetrafluoroborate, perchlorate, nitrate, sulfate, carbonate, and sulfite;
Y is an anion selected from chloride, bromide, iodide, fluoride, tetrafluoroborate, perchlorate, and nitrate;
n is 1 or 0;
with the proviso that if X is sulfate, carbonate, or sulfite, then n is 0;
and with the proviso that if m is +1 then n is 0, and X is not sulfate, carbonate, or sulfite;
and wherein the aqueous solubility of the compound of Formula I is greater than about 1 mM.
3. The mediator formulation according to embodiment 1 or 2, wherein the at least one osmium compound is [Os(III)(bpy)$_2$imCl]Cl$_2$.
4. The mediator formulation according to any one of embodiments 1-3, wherein the at least one ruthenium compound is a ruthenium hexammine complex.
5. The mediator formulation according to any one of embodiments 1-4, wherein the at least one ruthenium compound is ruthenium hexammine trichloride.

6. A mediator formulation for detecting an analyte, comprising [Os(III)(bpy)$_2$imCl]Cl$_2$ and ruthenium hexammine trichloride.
7. The mediator formulation according to any one of embodiments 1-6, wherein the at least one osmium compound, the compound of Formula I, or [Os(III)(bpy)$_2$ imCl]Cl$_2$ is present in a concentration from about 1 mM to about 50 mM.
8. The mediator formulation according to any one of embodiments 1-7, wherein the at least one osmium compound, the compound of Formula I, or [Os(III)(bpy)$_2$ imCl]Cl$_2$ is present in a concentration from about 1 mM to about 10 mM.
9. The mediator formulation according to any one of embodiments 1-8, wherein the at least one osmium compound, the compound of Formula I, or [Os(III)(bpy)$_2$ imCl]Cl$_2$ is present in a concentration of about 5 mM.
10. The mediator formulation according to any one of embodiments 1-9, wherein the at least one ruthenium compound, the ruthenium hexammine complex, or ruthenium hexammine trichloride is present in a concentration from about 100 mM to about 200 mM.
11. The mediator formulation according to any one of embodiments 1-10, wherein the at least one ruthenium compound, the ruthenium hexammine complex, or ruthenium hexammine trichloride is present in a concentration of about 150 mM.
12. A mediator formulation for detecting an analyte, comprising about 5 mM of [Os(III)(bpy)$_2$imCl]Cl$_2$ and about 150 mM of ruthenium hexammine trichloride.
13. The mediator formulation according to any one of embodiments 1-12, wherein the analyte is selected from glucose, cholesterol, hemoglobin A$_{1C}$, fructose, alcohol, lactate, triglycerides, creatine, creatinine, bilirubin, uric acid, amino acids, ketones, and coagulation factors.
14. The mediator formulation according to any one of embodiments 1-13, wherein the analyte is glucose.
15. A reagent formulation for detecting an analyte, comprising:
    a mediator formulation according to any one of embodiments 1-14; and
    an oxidoreductase optionally comprising a coenzyme and/or cofactor.
16. A reagent formulation for detecting an analyte, comprising:
    a mediator formulation comprising at least one osmium compound and at least one ruthenium compound; and
    an oxidoreductase optionally comprising a coenzyme and/or cofactor.
17. The reagent formulation according to embodiment 15 or 16, wherein the oxidoreductase is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase.
18. The reagent formulation according to any one of embodiments 15-17, wherein the oxidoreductase is a glucose oxidoreductase.
19. A reagent formulation for detecting an analyte, comprising:
    a mediator formulation comprising at least one osmium compound and at least one ruthenium compound; and
    a glucose oxidoreductase optionally comprising a coenzyme and/or cofactor.
20. The reagent formulation according to any one of embodiments 15-19, wherein the oxidoreductase is glucose dehydrogenase (GDH).
21. The reagent formulation according to any one of embodiments 15-20, wherein the oxidoreductase is glucose oxidase (GOX).
22. The reagent formulation according to any one of embodiments 15-21, wherein the oxidoreductase comprises a coenzyme selected from flavin nucleoside and nicotinamide nucleotide.
23. A reagent formulation for detecting an analyte, comprising:
    a mediator formulation comprising at least one osmium compound and at least one ruthenium compound; and
    a glucose oxidoreductase comprising a coenzyme selected from flavin nucleoside and nicotinamide nucleotide.
24. The reagent formulation according to any one of embodiments 15-23, wherein the coenzyme is flavin adenine dinucleotide (FAD).
25. The reagent formulation according to any one of embodiments 15-23, wherein the coenzyme is nicotinamide adenine dinucleotide(phosphate) (NAD(P)).
26. The reagent formulation according to any one of embodiments 15-25, wherein the oxidoreductase comprising a coenzyme is selected from flavin adenine dinucleotide-dependent glucose dehydrogenase (FAD-GDH), nicotinamide adenine dinucleotide(phosphate)-dependent glucose dehydrogenase (NAD(P)-GDH), and glucose oxidase (GOX).
27. The reagent formulation according to any one of embodiments 15-26, wherein the oxidoreductase comprising a coenzyme is flavin adenine dinucleotide-dependent glucose dehydrogenase (FAD-GDH).
28. The reagent formulation according to any one of embodiments 15-26, wherein the oxidoreductase comprising a coenzyme is nicotinamide adenine dinucleotide (phosphate)-dependent glucose dehydrogenase (NAD(P)-GDH).
29. The reagent formulation according to any one of embodiments 15-26, wherein the oxidoreductase comprising a coenzyme is glucose oxidase (GOX).
30. The reagent formulation according to any one of embodiments 15-29, wherein the analyte is selected from glucose, cholesterol, hemoglobin A$_{1C}$, fructose, alcohol, lactate, triglycerides, creatine, creatinine, bilirubin, uric acid, amino acids, ketones, and coagulation factors.
31. The reagent formulation according to any one of embodiments 15-30, wherein the analyte is glucose.
32. A reagent formulation for detecting glucose, comprising:
    a mediator formulation,
        wherein said mediator formulation comprises [Os(III) (bpy)$_2$imCl]Cl$_2$ and ruthenium hexammine trichloride; and
    an oxidoreductase optionally comprising a coenzyme and/or cofactor, wherein said oxidoreductase is FAD-GDH.
33. A reagent formulation for detecting glucose, comprising:
    a mediator formulation,
        wherein said mediator formulation comprises [Os(III) (bpy)$_2$imCl]Cl$_2$ and ruthenium hexammine trichloride; and
    an oxidoreductase optionally comprising a coenzyme and/or cofactor, wherein said oxidoreductase is GOX.
34. The reagent formulation according to any one of embodiments 15-33, wherein the oxidoreductase optionally comprising a coenzyme and/or cofactor is present in a concentration from about 1,000 U/mL to about 25,000 U/mL.
35. The reagent formulation according to any one of embodiments 15-34, wherein the oxidoreductase optionally comprising a coenzyme and/or cofactor is present in a concentration from about 5,000 U/mL to about 15,000 U/mL
36. The reagent formulation according to any one of embodiments 15-35, wherein the oxidoreductase optionally comprising a coenzyme and/or cofactor is present in a concentration from about 8,000 U/mL to about 12,000 U/mL.
37. The reagent formulation according to any one of embodiments 15-36, wherein the oxidoreductase optionally comprising a coenzyme and/or cofactor is present in a concentration of about 10,000 U/mL.
38. The reagent formulation according to any of embodiments 15-37, wherein said reagent formulation further comprises one or more of the following: at least one buffer, at least one thickening agent, and at least one surfactant.
39. The reagent formulation according to any one of embodiments 15-38, further comprising at least one buffer.
40. The reagent formulation according to embodiment 39, wherein said buffer is phosphate buffer.
41. The reagent formulation according to embodiment 39 or 40, wherein said buffer is present in a concentration from about 10 mM to about 250 mM.
42. The reagent formulation according to any one of embodiments 39-41, wherein said buffer is present in a concentration from about 25 mM to about 75 mM.
43. The reagent formulation according to any one of embodiments 39-42, wherein said buffer is present in a concentration of about 50 mM.
44. The reagent formulation according to any one of embodiments 15-43, further comprising at least one thickening agent.
45. The reagent formulation according to embodiment 44, wherein said thickening agent is hydroxypropyl methyl cellulose.
46. The reagent formulation according to embodiment 44 or 45, wherein said thickening agent is present in a concentration from about 0% w/v to about 5% w/v.
47. The reagent formulation according to any one of embodiments 44-46, wherein said thickening agent is present in a concentration from about 0% w/v to about 1% w/v.
48. The reagent formulation according to any one of embodiments 44-47, wherein said thickening agent is present in a concentration of about 0.25% w/v.
49. The reagent formulation according to any one of embodiments 15-48, further comprising at least one surfactant.
50. The reagent formulation according to embodiment 49, wherein said surfactant is Triton X-100.
51. The reagent formulation according to embodiment 49 or 50, wherein said surfactant is present in a concentration from about 0% v/v to about 1% v/v.
52. The reagent formulation according to any one of embodiments 49-51, wherein said surfactant is present in a concentration from about 0% v/v to about 0.5% v/v.
53. The reagent formulation according to any one of embodiments 49-52, wherein said surfactant is present in a concentration from about 0% v/v to about 0.1% v/v.
54. The reagent formulation according to any one of embodiments 49-53, wherein said surfactant is present in a concentration of about 0.06% v/v.
55. A reagent formulation for detecting an analyte, comprising:
    (i) a buffer;
    (ii) an oxidoreductase optionally comprising a coenzyme and/or cofactor;
    (iii) a ruthenium compound;
    (iv) an osmium compound;
    (v) a thickening agent; and
    (vi) a surfactant.
56. A reagent formulation for detecting an analyte, comprising:
    (i) a buffer;
    (ii) an oxidoreductase optionally comprising a coenzyme and/or cofactor;
    (iii) ruthenium hexammine trichloride;
    (iv) an osmium compound;
    (v) a thickening agent; and
    (vi) a surfactant;
    wherein said osmium compound is a compound of Formula I:

$$\left[ \begin{array}{c} R'' \\ | \\ N \\ \diagdown \\ N \\ R \diagup\kern-0.5em\diagdown Os \diagdown\kern-0.5em\diagup Z \\ | \\ R' \end{array} \right]_m XY_n$$

Formula I wherein:
    R and R' are the same or different and are selected from 2,2'-bipyridyl, 4,4'-disubstituted-2,2'-bipyridyl, 5,5'-disubstituted-2,2'-bipyridyl, 1,10-phenanthrolinyl, 4,7-disubstituted-1,10-phenanthrolinyl, and 5,6-disubstituted-1,10-phenanthrolinyl, wherein the disubstitution is a methyl, ethyl, or phenyl group;
    R and R' are coordinated to Os at their nitrogen atoms;
    R" is selected from hydrogen, methyl, and ethyl;
    Z is chloro or bromo;
    m is +1 or +2;
    X is an anion selected from chloride, bromide, iodide, fluoride, tetrafluoroborate, perchlorate, nitrate, sulfate, carbonate, and sulfite;
    Y is an anion selected from chloride, bromide, iodide, fluoride, tetrafluoroborate, perchlorate, and nitrate;
    n is 1 or 0;
    with the proviso that if X is sulfate, carbonate, or sulfite, then n is 0;
    and with the proviso that if m is +1 then n is 0, and X is not sulfate, carbonate, or sulfite;
    and wherein the aqueous solubility of the compound of Formula I is greater than about 1 mM.
57. A reagent formulation for detecting an analyte, comprising:
    (i) a buffer;
    (ii) an oxidoreductase optionally comprising a coenzyme and/or cofactor;
    (iii) ruthenium hexammine trichloride;

(iv) [Os(III)(bpy)₂imCl]Cl₂;
(v) a thickening agent; and
(vi) a surfactant.

58. The reagent formulation according to embodiment 57, comprising:
   (i) about 10 mM to about 250 mM buffer;
   (ii) about 1,000 U/mL to about 25,000 U/mL oxidoreductase optionally comprising a coenzyme and/or cofactor;
   (iii) about 100 mM to about 200 mM ruthenium hexammine trichloride;
   (iv) about 1 mM to about 50 mM, [Os(III)(bpy)₂imCl]Cl₂;
   (v) about 0% w/v to about 5% w/v thickening agent; and
   (vi) about 0% v/v to about 1% v/v surfactant.

59. The reagent formulation according to embodiment 57 or 58, comprising:
   (i) about 10 mM to about 250 mM buffer;
   (ii) about 10,000 U/mL oxidoreductase optionally comprising a coenzyme and/or cofactor;
   (iii) about 150 mM ruthenium hexammine trichloride;
   (iv) about 1 mM to about 10 mM [Os(III)(bpy)₂imCl]Cl₂;
   (v) about 0% w/v to about 1% w/v thickening agent; and
   (vi) about 0% v/v to about 0.5% v/v surfactant.

60. The reagent formulation according to any one of embodiments 57-59, comprising:
   (i) about 50 mM buffer;
   (ii) about 10,000 U/mL oxidoreductase optionally comprising a coenzyme and/or cofactor;
   (iii) about 150 mM ruthenium hexammine trichloride;
   (iv) about 1 mM to about 10 mM [Os(III)(bpy)₂imCl]Cl₂;
   (v) about 0.25% w/v thickening agent; and
   (vi) about 0.06% v/v surfactant.

61. The reagent formulation according to any one of embodiments 57-60, comprising:
   (i) about 50 mM buffer;
   (ii) about 10,000 U/mL oxidoreductase optionally comprising a coenzyme and/or cofactor;
   (iii) about 150 mM ruthenium hexammine trichloride;
   (iv) about 5 mM [Os(III)(bpy)₂imCl]Cl₂;
   (v) about 0.25% w/v thickening agent; and
   (vi) about 0.06% v/v surfactant.

62. A reagent formulation for detecting glucose, comprising:
   (i) phosphate buffer;
   (ii) flavin adenine dinucleotide-dependent glucose dehydrogenase (FAD-GDH); (iii) ruthenium hexammine trichloride;
   (iv) [Os(III)(bpy)₂imCl]Cl₂;
   (v) hydroxypropyl methylcellulose; and
   (vi) Triton X-100.

63. The reagent formulation according to embodiment 62, comprising:
   (i) about 10 mM to about 250 mM phosphate buffer;
   (ii) about 1,000 U/mL to about 25,000 U/mL flavin adenine dinucleotide-dependent glucose dehydrogenase (FAD-GDH);
   (iii) about 100 mM to about 200 mM ruthenium hexammine trichloride;
   (iv) about 1 mM to about 50 mM, [Os(III)(bpy)₂imCl]Cl₂;
   (v) about 0% w/v to about 5% w/v hydroxypropyl methylcellulose; and
   (vi) about 0% v/v to about 1% v/v Triton X-100.

64. The reagent formulation according to embodiment 62 or 63, comprising:
   (i) about 10 mM to about 250 mM phosphate buffer;
   (ii) about 10,000 U/mL flavin adenine dinucleotide-dependent glucose dehydrogenase (FAD-GDH);
   (iii) about 150 mM ruthenium hexammine trichloride;
   (iv) about 1 mM to about 10 mM [Os(III)(bpy)₂imCl]Cl₂;
   (v) about 0% w/v to about 1% w/v hydroxypropyl methylcellulose; and
   (vi) about 0% v/v to about 0.5% v/v Triton X-100.

65. The reagent formulation according to any one of embodiments 62-64, comprising:
   (i) about 50 mM phosphate buffer;
   (ii) about 10,000 U/mL flavin adenine dinucleotide-dependent glucose dehydrogenase (FAD-GDH);
   (iii) about 150 mM ruthenium hexammine trichloride;
   (iv) about 1 mM to about 10 mM [Os(III)(bpy)₂imCl]Cl₂;
   (v) about 0.25% w/v hydroxypropyl methylcellulose; and
   (vi) about 0.06% v/v Triton X-100.

66. The reagent formulation according to any one of embodiments 62-65, comprising:
   (i) about 50 mM phosphate buffer;
   (ii) about 10,000 U/mL flavin adenine dinucleotide-dependent glucose dehydrogenase (FAD-GDH);
   (iii) about 150 mM ruthenium hexammine trichloride;
   (iv) about 5 mM [Os(III)(bpy)₂imCl]Cl₂;
   (v) about 0.25% w/v hydroxypropyl methylcellulose; and
   (vi) about 0.06% v/v Triton X-100.

67. A reagent formulation for detecting glucose, comprising:
   (i) phosphate buffer;
   (ii) glucose oxidase (GOX);
   (iii) ruthenium hexammine trichloride;
   (iv) [Os(III)(bpy)₂imCl]Cl₂;
   (v) hydroxypropyl methylcellulose; and
   (vi) Triton X-100.

68. The reagent formulation according to embodiment 67, comprising:
   (i) about 10 mM to about 250 mM phosphate buffer;
   (ii) about 1,000 U/mL to about 25,000 U/mL glucose oxidase (GOX);
   (iii) about 100 mM to about 200 mM ruthenium hexammine trichloride;
   (iv) about 1 mM to about 50 mM, [Os(III)(bpy)₂imCl]Cl₂;
   (v) about 0% w/v to about 5% w/v hydroxypropyl methylcellulose; and
   (vi) about 0% v/v to about 1% v/v Triton X-100.

69. The reagent formulation according to embodiment 67 or 68, comprising:
   (i) about 10 mM to about 250 mM phosphate buffer;
   (ii) about 10,000 U/mL glucose oxidase (GOX);
   (iii) about 150 mM ruthenium hexammine trichloride;
   (iv) about 1 mM to about 10 mM [Os(III)(bpy)₂imCl]Cl₂;
   (v) about 0% w/v to about 1% w/v hydroxypropyl methylcellulose; and
   (vi) about 0% v/v to about 0.5% v/v Triton X-100.

70. The reagent formulation according to any one of embodiments 67-69, comprising:
   (i) about 50 mM phosphate buffer;
   (ii) about 10,000 U/mL glucose oxidase (GOX);
   (iii) about 150 mM ruthenium hexammine trichloride;
   (iv) about 1 mM to about 10 mM [Os(III)(bpy)₂imCl]Cl₂;
   (v) about 0.25% w/v hydroxypropyl methylcellulose; and
   (vi) about 0.06% v/v Triton X-100.

71. The reagent formulation according to any one of embodiments 67-70, comprising:
   (i) about 50 mM phosphate buffer;
   (ii) about 10,000 U/mL glucose oxidase (GOX);
   (iii) about 150 mM ruthenium hexammine trichloride;
   (iv) about 5 mM [Os(III)(bpy)₂imCl]Cl₂;
   (v) about 0.25% w/v hydroxypropyl methylcellulose; and
   (vi) about 0.06% v/v Triton X-100.

72. The reagent formulation according to any one of embodiments 15-71, wherein the pH of said reagent formulation is in a range from about 2.0 to about 11.0.

73. The reagent formulation according to any one of embodiments 15-72, wherein the pH of said reagent formulation is in a range from about 5.7 to about 8.0.
74. The reagent formulation according to any one of embodiments 15-73, wherein the pH of said reagent formulation is in a range from about 6.0 to about 7.0.
75. The reagent formulation according to any one of embodiments 15-74, wherein the pH of said reagent formulation is about 6.3.
76. A reagent formulation for detecting an analyte, comprising:
    (i) about 50 mM buffer;
    (ii) about 10,000 U/mL oxidoreductase optionally comprising a coenzyme and/or cofactor;
    (iii) about 150 mM ruthenium hexammine trichloride;
    (iv) about 1 mM to about 10 mM $[Os(III)(bpy)_2imCl]Cl_2$;
    (v) about 0.25% w/v thickening agent; and
    (vi) about 0.06% v/v surfactant;
    wherein the pH of said reagent formulation is about 6.3.
77. A reagent formulation for detecting glucose, comprising:
    (i) about 50 mM phosphate buffer;
    (ii) about 10,000 U/mL flavin adenine dinucleotide-dependent glucose dehydrogenase (FAD-GDH);
    (iii) about 150 mM ruthenium hexammine trichloride;
    (iv) about 5 mM $[Os(III)(bpy)_2imCl]Cl_2$;
    (v) about 0.25% w/v hydroxypropyl methylcellulose; and
    (vi) about 0.06% v/v Triton X-100;
    wherein the pH of said reagent formulation is about 6.3.
78. A reagent formulation for detecting glucose, comprising:
    (i) about 50 mM phosphate buffer;
    (ii) about 10,000 U/mL glucose oxidase (GOX);
    (iii) about 150 mM ruthenium hexammine trichloride;
    (iv) about 5 mM $[Os(III)(bpy)_2imCl]Cl_2$;
    (v) about 0.25% w/v hydroxypropyl methylcellulose; and
    (vi) about 0.06% v/v Triton X-100;
    wherein the pH of said reagent formulation is about 6.3.
79. The reagent formulation according to any one of embodiments 15-78, further comprising at least one enzyme stabilizer.
80. An electrochemical sensor strip, comprising:
    a base;
    at least one working electrode;
    at least one counter electrode; and
    at least one reagent layer;
    wherein said at least one reagent layer comprises a mediator formulation according to any one of embodiments 1-14 or a reagent formulation according to any of embodiments 15-79.
81. A method of making an electrochemical sensor strip, comprising:
    applying at least one first electrode on a base;
    applying at least one second electrode on the base; and
    applying a reagent layer on the base covering at least a portion of at least first or second electrode;
    wherein said at least one reagent layer comprises a mediator formulation according to any one of embodiments 1-14 or a reagent formulation according to any of embodiments 15-79.
82. A meter for use in combination with a test strip for measuring a glucose level in a blood sample applied to a test strip, said test strip comprising a base, at least one working electrode, at least one counter electrode, and at least one reagent layer, wherein the at least one reagent layer comprises a mediator formulation according to any one of embodiments 1-14 or a reagent formulation according to any of embodiments 15-79, said meter comprising:
    a port for receiving said test strip;
    a processor;
    a display; and
    at least one voltage source for applying at least a first voltage between said working and counter electrodes when said test strip is inserted.
83. A continuous glucose monitoring system, comprising:
    at least one sensor configured to detect one or more glucose levels, wherein said sensor detects one or more glucose levels via a mediator formulation according to any one of embodiments 1-14;
    at least one transmitter, wherein said transmitter is coupled to the sensor to detect one or more glucose levels, and wherein the transmitter periodically transmits signals corresponding to one or more detected glucose levels; and
    at least one receiver, wherein said receiver is coupled to the transmitter to receive the transmitted signals corresponding to one or more detected glucose levels.
84. A continuous glucose monitoring system, comprising:
    at least one sensor configured to detect one or more glucose levels, wherein said sensor detects one or more glucose levels via a reagent formulation according to any one of embodiments 15-79;
    at least one transmitter, wherein said transmitter is coupled to the sensor to detect one or more glucose levels, and wherein the transmitter periodically transmits signals corresponding to one or more detected glucose levels; and
    at least one receiver, wherein said receiver is coupled to the transmitter to receive the transmitted signals corresponding to one or more detected glucose levels
85. The mediator formulation according to any one of embodiments 1-14, for use in a continuous glucose monitoring system, comprising:
    at least one sensor configured to detect one or more glucose levels;
    at least one transmitter, wherein said transmitter is coupled to the sensor to detect one or more glucose levels, and wherein the transmitter periodically transmits signals corresponding to one or more detected glucose levels; and
    at least one receiver, wherein said receiver is coupled to the transmitter to receive the transmitted signals corresponding to one or more detected glucose levels.
86. The reagent formulation according to any of embodiments 15-79, for use in a continuous glucose monitoring system, comprising:
    at least one sensor configured to detect one or more glucose levels;
    at least one transmitter, wherein said transmitter is coupled to the sensor to detect one or more glucose levels, and wherein the transmitter periodically transmits signals corresponding to one or more detected glucose levels; and
    at least one receiver, wherein said receiver is coupled to the transmitter to receive the transmitted signals corresponding to one or more detected glucose levels.

EXAMPLES

Example 1: Preparation of Reagent Formulation

A buffer solution was prepared by dissolving 4.355 g dibasic potassium phosphate (Alfa Aesar) and 1.250 g hydroxypropyl methylcellulose (Alfa Aesar) in 500 mL deionized water. The pH was adjusted to 6.30 and 283 µL Triton X-100 was added.

Mediator formulations were prepared by dissolving appropriate amounts of a ruthenium compound and an osmium compound in the above buffer solution to achieve the desired concentration. For example, to achieve 150 mM of $Ru(NH_3)_6Cl_3$ and 5 mM of $[Os(III)(bpy)_2imCl]Cl_2$, 0.4644 g of $Ru(NH_3)_6Cl_3$ and 0.0339 g of $[Os(III)(bpy)_2imCl]Cl_2$ were dissolved in 10 mL of the above buffer solution. The various concentrations of $Ru(NH_3)_6Cl_3$ and $[Os(III)(bpy)_2imCl]Cl_2$ prepared and used for testing are listed in the table below:

TABLE 1

Concentrations of $Ru(NH_3)_6Cl_3$ and $[Os(III)(bpy)_2imCl]Cl_2$

| $Ru(NH_3)_6Cl_3$ concentration | $[Os(III)(bpy)_2imCl]Cl_2$ concentration |
| --- | --- |
| 150 mM | 0 mM |
| 150 mM | 1 mM |
| 150 mM | 2 mM |
| 150 mM | 5 mM |
| 150 mM | 10 mM |
| 0 mM | 25 mM |
| 0 mM | 150 mM |

Regent formulations were prepared by dissolving appropriate amounts of an oxidoreductase in the above mediator solution. For example, to achieve 10,000 U/mL of FAD-dependent glucose dehydrogenase, 0.0258 g (10,000 U) of FAD-dependent glucose dehydrogenase (Toyobo) was dissolved in 1 mL of the above mediator solution prior to preparation of test strips. Reagent formulations were also prepared with glucose oxidase, following a similar procedure.

Example 2: Preparation of Test Strips 0.8 µL of the reagent formulation from Example 1 was dispensed into the sample chamber of each strip in a 50-strip array. The strip array was then dried in a convection oven at 50° C. for 4 minutes. The strip array was then laminated with a hydrophilic clear cover using a hot roller laminator heated to 270° C. The strip array was then cut into individual test strips, which were stored in desiccated vials until use.

Example 3: Glucose Dose Response

Glucose dose response of the reagent formulation was measured using control solutions at the following levels of glucose: 0, 50, 100, 240, 350, and 600 mg/dL. Glucose measurements were taken with a 12-meter test stand controlled by a computer through USB connection.

For each glucose level, test strips were inserted into the strip connector, and the appropriate glucose control solution was applied to the sample chamber of each test strip. The electrochemical measurement began once the sample was detected. The resulting dose response for glucose concentrations ranging from 0 to 600 mg/dL is shown in FIG. 1 for FAD-dependent glucose dehydrogenase (FAD-GDH).

Example 4: Oxygen Dependence Measurements and Glucose Dose Response

Oxygen dependence was measured using samples of venous whole blood, which were divided into two portions. One portion was kept as is and sealed airtight (e.g., 37 mmHg), while the other portion was oxygenated to a desired $pO_2$ level (e.g., 120 mmHg, 215 mmHg, or 226 mmHg). The $pO_2$ values for all blood samples were measured using a blood gas analyzer (OPTI Medical Systems, Inc.).

Blood samples at each $pO_2$ level were further divided into 5 aliquots and spiked with glucose to target a range of glucose concentrations from 100 to 550 mg/dL. Actual glucose levels for each aliquot were assayed using an YSI glucose analyzer (Yellow Springs Instruments).

Figure 7:
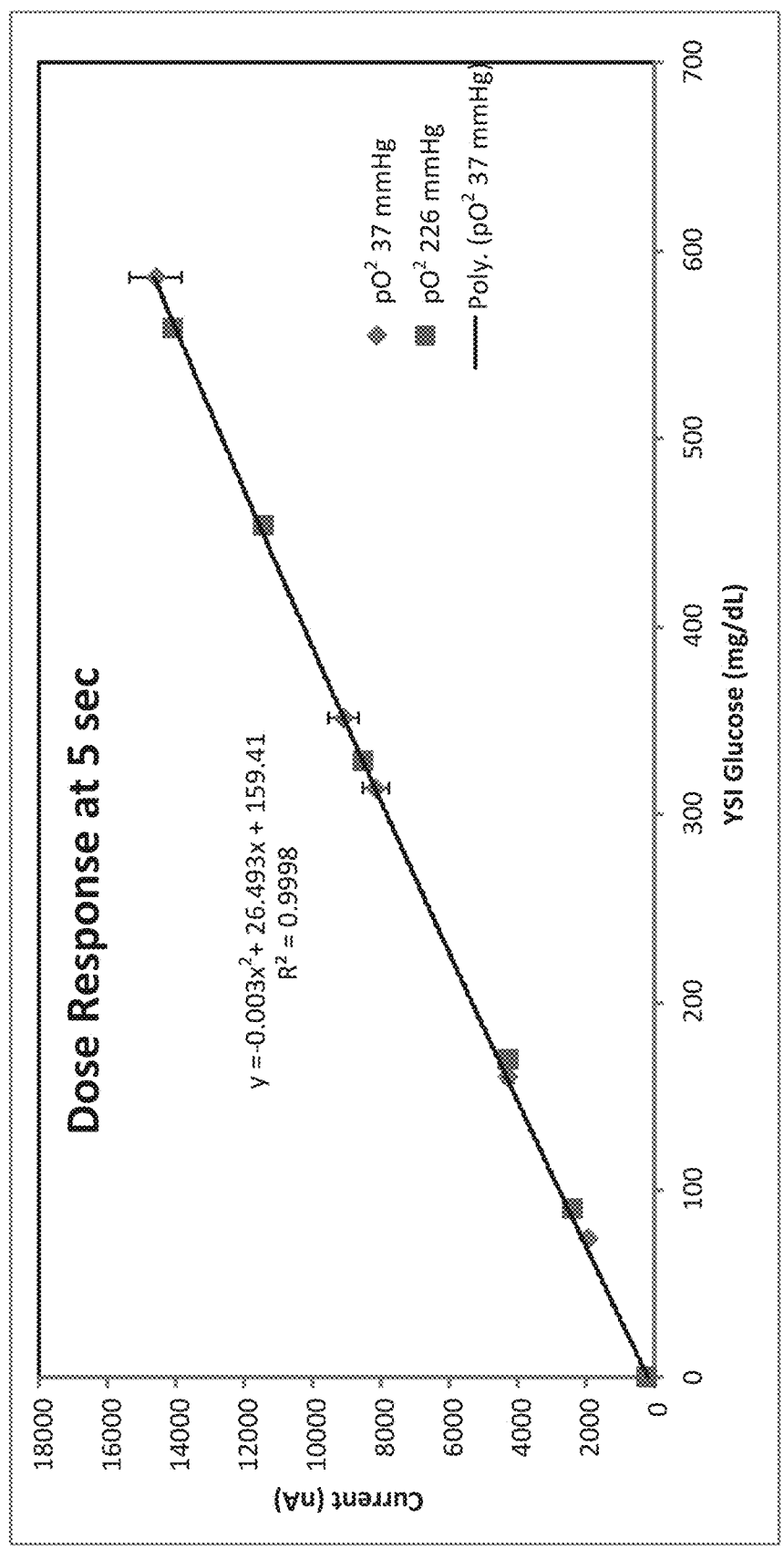
FIG. 7 is a dose response curve for reagent formulation comprising FAD-GDH and a multi-mediator formulation comprising 150 mM of Ru(NH$_3$)$_6$Cl$_3$ and 5 mM of [Os(III)(bpy)$_2$imCl]Cl$_2$ at pO$_2$ values of 37 mm Hg and 226 mm Hg.
Figure 8:
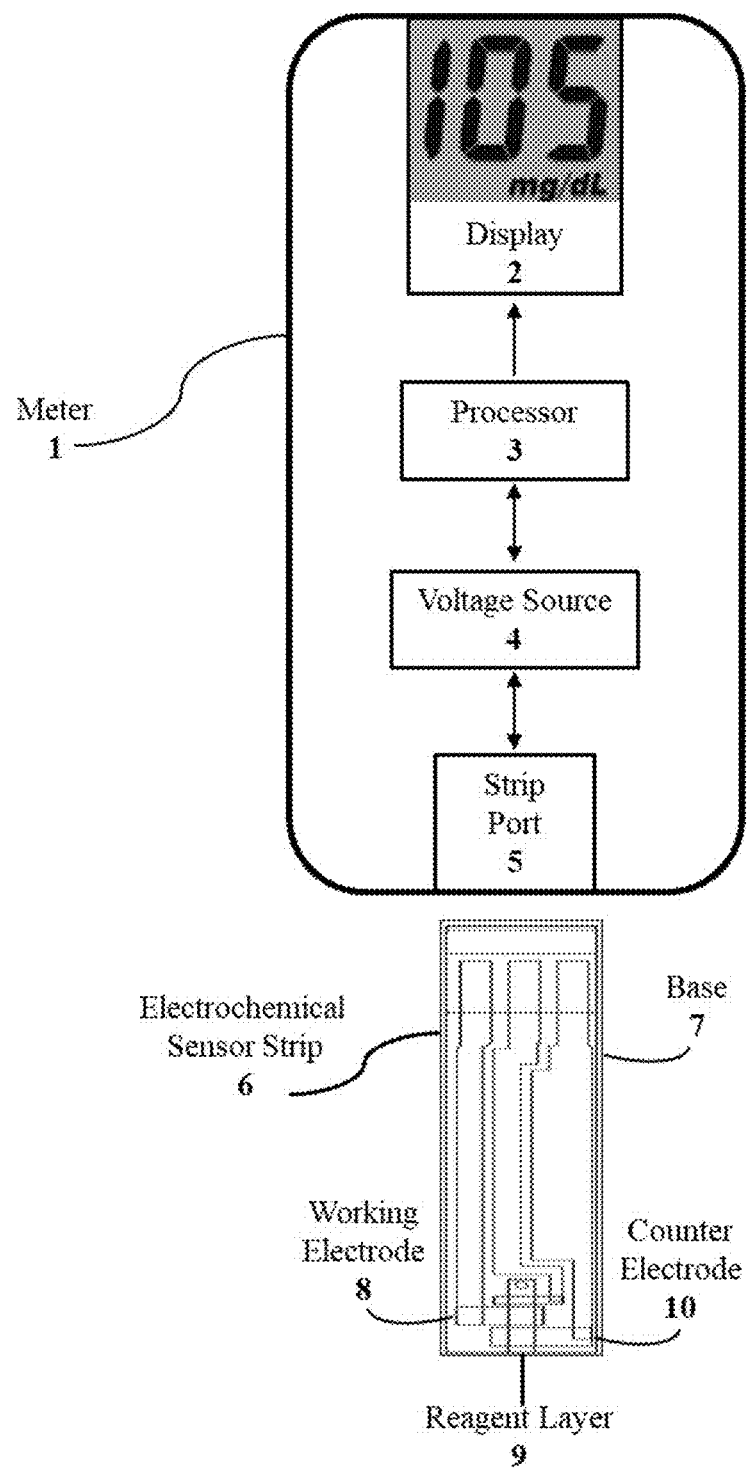
FIG. 8 depicts an embodiment of a meter 1 for use in combination with a electrochemical sensor strip 6, wherein said meter 1 comprises a port for receiving said test strip 5, a processor 3, a display 2, and at least one voltage source 4, and wherein said electrochemical sensor strips 6 comprises at least one working electrode 8, at least one counter electrode 10, and at least one reagent layer 9.
Figure 9:
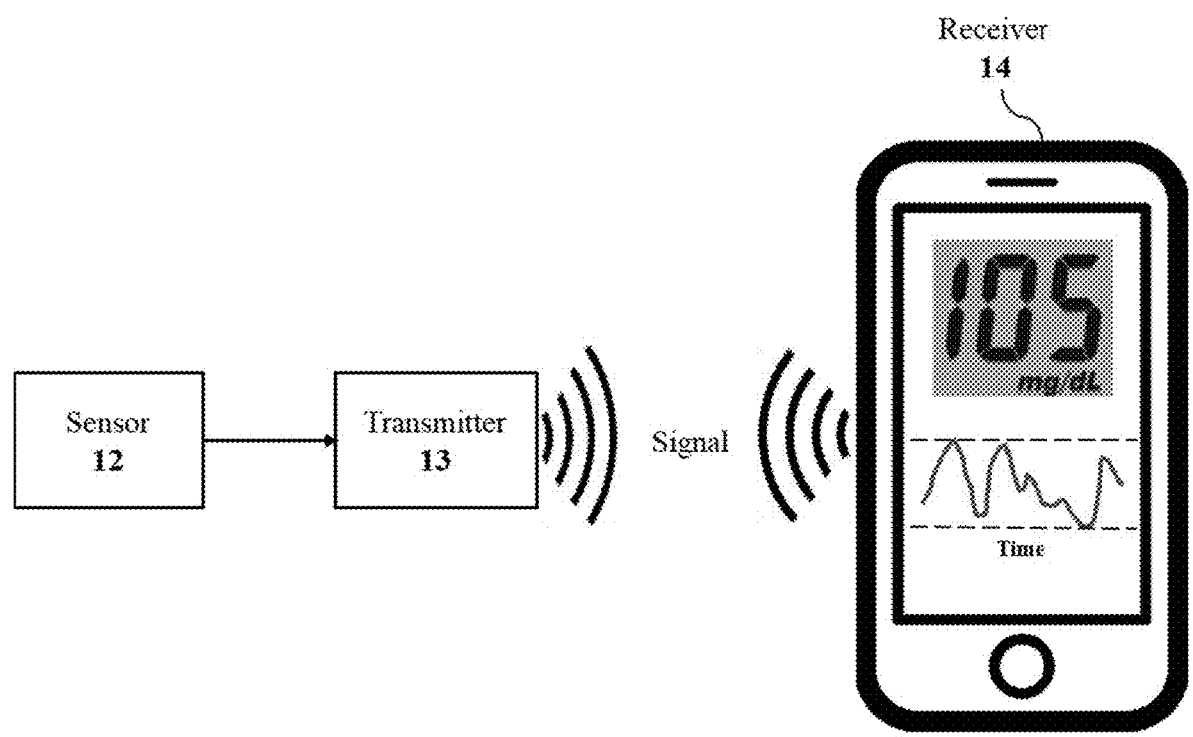
FIG. 9 depicts an embodiment of a continuous glucose monitoring system 11 comprising at least one sensor 12 configured to detect one or more glucose levels via a mediator formulation, at least one transmitter 13 coupled to the at least one sensor 12, wherein transmitter transmits signals corresponding to one or more detected glucose levels, and at least one receiver 14 coupled to the transmitter to receive the transmitted signals corresponding to one or more glucose levels.

The blood samples were then applied to test strips, and the glucose concentration was measured according to the procedure described in Example 3 to generate a glucose dose response as shown in FIG. 5 for glucose oxidase and FIG. 7 for FAD-dependent glucose dehydrogenase. The bias plot for test strip readings (average bias for 10 test strips) compared to the actual glucose levels (YSI readings) is shown in FIG. 4 for glucose oxidase and FIG. 6 for FAD-dependent glucose dehydrogenase.

Other embodiments of the invention will be apparent to those skilled in the art from consideration of the specification and practice of the invention disclosed herein. It is intended that the specification and examples be considered as exemplary only, with a true scope and spirit of the invention being indicated by the claims.

What is claimed is:

1. A mediator formulation for detecting an analyte, comprising: ruthenium hexammine trichloride and $[Os(III)(bpy)_2imCl]Cl_2$, wherein:
   the $[Os(III)(bpy)_2imCl]Cl_2$ is present in a concentration from about 1 mM to about 10 mM; and
   the ruthenium hexammine trichloride is present in a concentration from about 100 mM to about 200 mM.

2. A reagent formulation for detecting an analyte, comprising:
   the mediator formulation according to claim 1; and
   an oxidoreductase optionally comprising a coenzyme and/or cofactor.

3. The reagent formulation according to claim 2, wherein the oxidoreductase optionally comprising a coenzyme and/or cofactor is selected from glucose dehydrogenase, glucose oxidase, bilirubin oxidase, fructosyl amino acid oxidase, fructosyl peptide oxidase, neutral proteinase, alcohol dehydrogenase, alcohol oxidase, cholesterol esterase, lipoprotein lipase, glyceral kinase, galactose oxidase, lactate oxidase, lactate dehydrogenase, pyruvate oxidase, and uricase.

4. The reagent formulation according to claim 3, wherein the oxidoreductase is selected from flavin adenine dinucleotide-dependent glucose dehydrogenase (FAD-GDH), nicotinamide adenine dinucleotide(phosphate)-dependent glucose dehydrogenase (NAD(P)-GDH), and glucose oxidase (GOX).

5. The mediator formulation according to claim 1, wherein:
   the $[Os(III)(bpy)_2imCl]Cl_2$ is present in a concentration of about 5 mM; and
   the ruthenium hexammine trichloride is present in a concentration of about 150 mM.

6. A reagent formulation for detecting an analyte, comprising:
   the mediator formulation according to claim 5; and
   an oxidoreductase optionally comprising a coenzyme and/or cofactor.

7. A reagent formulation for detecting glucose, comprising:
   a mediator formulation comprising $[Os(III)(bpy)_2imCl]Cl_2$ and ruthenium hexammine trichloride;

an oxidoreductase selected from flavin adenine dinucleotide-dependent glucose dehydrogenase (FAD-GDH) and glucose oxidase (GOX);
at least one buffer;
at least one thickening agent; and
at least one surfactant, wherein the reagent formulation comprises:
(i) about 10 mM to about 50 mM of the at least one buffer;
(ii) about 1,000 U/mL to about 25,000 U/mL of the oxidoreductase selected from flavin adenine dinucleotide-dependent glucose dehydrogenase (FAD-GDH) and glucose oxidase (GOX);
(iii) about 100 mM to about 200 mM of the ruthenium hexammine trichloride;
(iv) about 1 to about 10 mM of the [Os(III)(bpy)$_2$imCl]Cl$_2$;
(v) about 0.25% w/v of the at least one thickening agent; and
(vi) about 0.06% v/v of the at least one surfactant.

8. The reagent formulation according to claim 7, wherein the at least one buffer is phosphate buffer, the at least one thickening agent is hydroxypropyl methyl cellulose, and the at least one surfactant is Triton X-100.

9. The reagent formulation according to claim 8, comprising:
(i) about 50 mM of the phosphate buffer;
(ii) about 10,000 U/m L of the oxidoreductase selected from flavin adenine dinucleotide-dependent glucose dehydrogenase (FAD-GDH) and glucose oxidase (GOX);
(iii) about 150 mM of the ruthenium hexammine trichloride;
(iv) about 5 mM of the [Os(III)(bpy)$_2$imCl]Cl$_2$;
(v) about 0.25% w/v of the hydroxypropyl methylcellulose; and
(vi) about 0.06% v/v of the Triton X-100.

10. The reagent formulation according to claim 9, wherein the pH of said reagent formulation is in the range of about 5.7 to about 8.0.

11. The reagent formulation according to claim 10, wherein the pH of said reagent formulation is about 6.3.

12. An electrochemical sensor strip, comprising:
a base;
at least one working electrode;
at least one counter electrode; and
at least one reagent layer;
wherein said at least one reagent layer comprises the reagent formulation according to claim 2.

13. A method of making an electrochemical sensor strip, comprising:
applying at least one first electrode on a base;
applying at least one second electrode on the base; and
applying a reagent layer on the base covering at least a portion of at least one of the at least one first electrode and at least one second electrode;
wherein said at least one reagent layer comprises the reagent formulation according to claim 2.

14. A meter with a test strip for measuring a glucose level in a blood sample applied to a test strip, said test strip comprising a base, at least one working electrode, at least one counter electrode, and at least one reagent layer, wherein the at least one reagent layer comprises the reagent formulation according to claim 2, said meter comprising:
a port for receiving said test strip;
a processor;
a display; and
at least one voltage source for applying at least a first voltage between said working and counter electrodes when said test strip is inserted.

15. A continuous glucose monitoring system, comprising:
at least one sensor configured to detect one or more glucose levels, wherein said sensor detects one or more glucose levels via the reagent formulation according to claim 2;
at least one transmitter, wherein said transmitter is coupled to the sensor to detect one or more glucose levels, and wherein the transmitter periodically transmits signals corresponding to the one or more detected glucose levels; and
at least one receiver, wherein said receiver is coupled to the transmitter to receive the transmitted signals corresponding to the one or more detected glucose levels.

* * * * *

UNITED STATES PATENT AND TRADEMARK OFFICE
CERTIFICATE OF CORRECTION

PATENT NO. : 10,781,469 B2
APPLICATION NO. : 15/173211
DATED : September 22, 2020
INVENTOR(S) : David Zhi Deng et al.

Page 1 of 1

It is certified that error appears in the above-identified patent and that said Letters Patent is hereby corrected as shown below:

In the Claims

In Claim 9, Column 37, Line 28, "U/m L" should read --U/mL--.

Signed and Sealed this
Twenty-seventh Day of October, 2020

Andrei Iancu
*Director of the United States Patent and Trademark Office*